United States Patent [19]
Voudouris

[11] Patent Number: 5,857,850
[45] Date of Patent: Jan. 12, 1999

[54] ORTHODONTIC APPLIANCE

[76] Inventor: John C. Voudouris, 16 Doon Road, Toronto, Canada, M2L 1L9

[21] Appl. No.: 625,944

[22] Filed: Apr. 1, 1996

Related U.S. Application Data

[63] Continuation-in-part of Ser. No. 412,338, Mar. 31, 1995, abandoned, which is a continuation-in-part of Ser. No. 206,724, Mar. 7, 1994, Pat. No. 5,474,445.

[30] Foreign Application Priority Data

Mar. 31, 1995 [GB] United Kingdom .................... 9506696

[51] Int. Cl.⁶ ..................................................... A61C 7/00
[52] U.S. Cl. .................................................. 433/11; 433/10
[58] Field of Search ........................ 433/10, 11, 13, 433/14, 8

[56] References Cited

U.S. PATENT DOCUMENTS

| | | | |
|---|---|---|---|
| 1,976,115 | 10/1934 | Boyd et al. | 433/11 |
| 3,091,857 | 6/1963 | Rubin et al. | 433/11 |
| 3,740,849 | 6/1973 | Rubin . | |
| 4,103,423 | 8/1978 | Kessel | 433/10 |
| 4,149,314 | 4/1979 | Nonnenmann | 433/13 |
| 4,419,078 | 12/1983 | Pletcher | 433/10 |
| 4,634,662 | 1/1987 | Rosenberg | 433/10 |
| 4,698,017 | 10/1987 | Hanson | 433/11 |
| 4,712,999 | 12/1987 | Rosenberg | 433/8 |
| 5,067,897 | 11/1991 | Tuneberg | 433/8 |
| 5,094,614 | 3/1992 | Wildman | 433/14 |
| 5,224,858 | 7/1993 | Hanson | 433/10 |
| 5,232,361 | 8/1993 | Sachdeva et al. | 433/8 |
| 5,269,681 | 12/1993 | Degnan | 433/11 |
| 5,275,557 | 1/1994 | Damon | 433/10 |
| 5,439,378 | 8/1995 | Damon | 433/8 |
| 5,474,446 | 12/1995 | Wildman et al. | 433/10 |

*Primary Examiner*—Cary E. O'Connor
*Attorney, Agent, or Firm*—Synnestvedt & Lechner

[57] ABSTRACT

In one embodiment, a pre-engaging orthodontic bracket includes a body having a lingual surface for attachment to a tooth, a pair of laterally spaced gingival tie wings and a pair of laterally spaced occlusal tie wings. The gingival and occlusal tie wings project from a labial surface of the body. An archwire slot extends mesiodistally across the body and between the gingival and occlusal tie wings at opposed mesial and distal sides of the body to accommodate an archwire. A pivot pin extends between a pair of the tie wings at opposed mesial and distal sides of the body. A shutter is moveable relative to the body between an open position in which placement and removal of an archwire into the archwire slot is facilitated and a closed position in which placement and removal of an archwire into the archwire slot is inhibited. The shutter includes a stem portion extending between the pair of tie wings and engages the pivot pin and a transverse arm portion at one end of the stem portion to engage the archwire slot when the shutter is in the closed position.

10 Claims, 37 Drawing Sheets

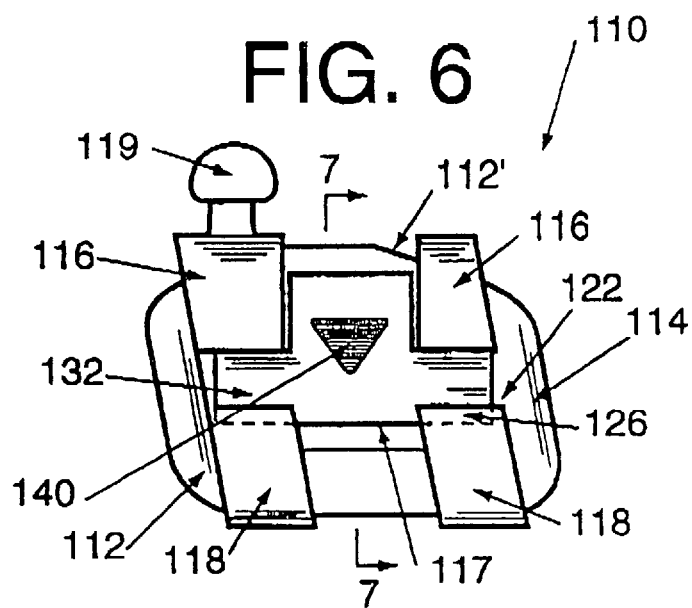
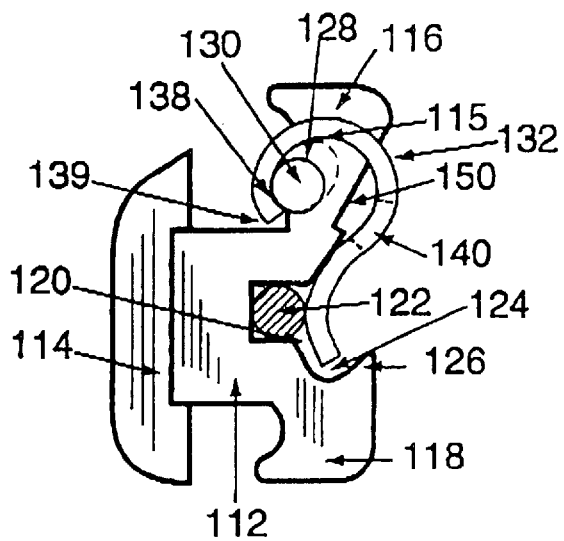

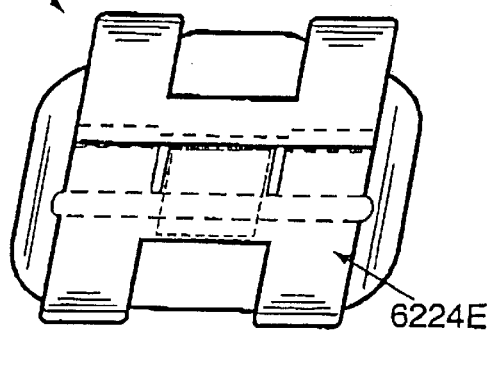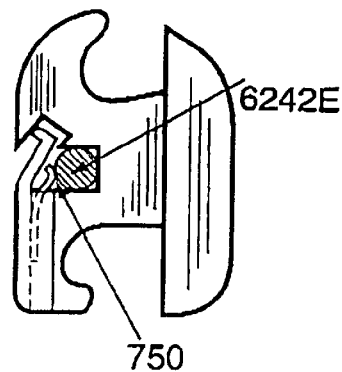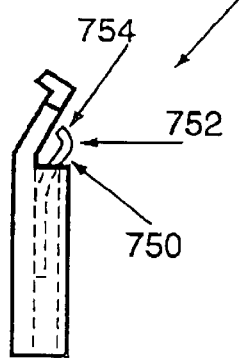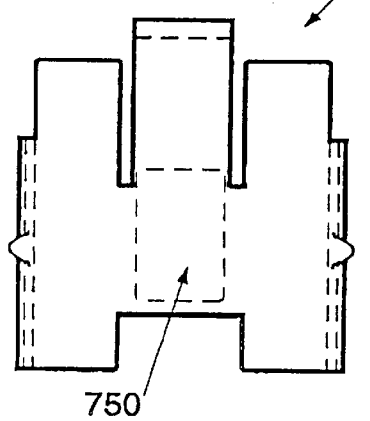

ORTHODONTIC APPLIANCE

RELATED APPLICATIONS

The present application is a continuation in part of U.S. application Ser. No. 08/412,338 filed on Mar. 31, 1995, now abandoned, which is a continuation-in-part of U.S. application Ser. No. 08/206,724 filed on Mar. 7, 1994 now issued and granted under U.S. Pat. No. 5,474,445.

FIELD OF THE INVENTION

The present invention relates in general to pre-engaging orthodontic brackets and in particular to a pre-engaging twin edgewise orthodontic bracket having a pivotal shutter.

BACKGROUND OF THE INVENTION

According to established orthodontic techniques, it is well known that one is able to ligate an archwire to a bracket utilizing an elastic, elastomeric or metal ligature. In a twin edgewise orthodontic bracket, the elastic ligature is stretched around respective undercuts of gingival and occlusal tie wings so as to overlay the archwire at mesial and distal ends of the bracket.

The ligating procedure involves carefully stretching the elastic or elastomeric ligature (or wrapping and twisting a metal ligature) around the tie wings utilizing appropriate orthodontic instruments. It has been found that the time-consuming ligation procedure contributes to lengthy chair time. Furthermore, the elastic ligatures are known to lose their elasticity with time and are subject to degradation. Also, the elastic and metal ligatures have been known to trap food particles in areas of the bracket which are difficult for the patient to clean, and to increase the level of friction against the archwire. Finally, the use of sharp metal ligatures around the bracket can subject the clinician to unnecessary exposure to infectious bacteria, or viruses such as hepatitis B, or possibly the HIV virus particularly in blood.

In an effort to overcome these disadvantages of elastic ligatures, certain advances have been made in the area of pre engaging orthodontic brackets. Each of U.S. Pat. Nos. 4,344,642; 4,248,588; 4,698,017; 3,772,787; 4,786,242; 4,559,012; 4,561,844; 4,655,708; 4,077,126; 4,419,078; 4,634,661; 4,197,642; and 4,712,999 illustrate one or more designs of pre-engaging brackets. These prior art devices overcome some of the disadvantages associated with elastic ligatures. For example, pre-engaging orthodontic brackets eliminate, or at least reduce, exposure of the clinician to sharp ligatures, thereby alleviating the problem of contracting harmful bacteria or viruses. In addition, pre-engaging orthodontic brackets permit continuous low deflection differential archwire contact separately for both round and rectangular archwires at at least two different levels of contact, which is not possible with degrading elastic, elastomeric or rigid, high deflection metal ligatures. However, most of the known prior art pre-engaging orthodontic brackets lack the reliability and the accessible ease of operability that most clinicians require. In addition, the majority of prior art pre-engaging orthodontic brackets are of a single design that have three or fewer tie wings.

It is therefore an object of the present invention to provide a novel twin pre-engaging orthodontic bracket which obviates or mitigates at least one of the above-identified disadvantages associated with prior art orthodontic brackets.

SUMMARY OF THE INVENTION

According to one aspect of the present invention there is provided an pre-engaging orthodontic bracket comprising:

a body having a lingual surface for attachment to a tooth, a pair of laterally spaced gingival tie wings and a pair of laterally spaced occlusal tie wings, said gingival and occlusal tie wings projecting from a labial surface of said body;

an archwire slot extending mesiodistally across said body and between the gingival and occlusal tie wings at opposed mesial and distal sides of said body to accommodate an archwire, said archwire slot being interrupted in an interwing region of said body;

a pivot pin extending between a pair of said tie wings at opposed mesial and distal sides of said body; and a shutter moveable relative to said body between an open position in which placement and removal of an archwire into said archwire slot is facilitated and a closed position in which placement and removal of an archwire into said archwire slot is inhibited, said shutter including a stem portion extending between said pair of tie wings and engaging said pivot pin and a transverse arm portion at one end of said stem portion to engage said archwire slot when said shutter is in said closed position.

In a preferred embodiment, the pivot pin extends between the gingival tie wings and the shutter resembles an inverted "T" in front elevation. It is also preferred that the orthodontic bracket further comprising retaining means to hold the shutter in the open position. In one embodiment, the body has a curved interwing gingival surface between the gingival tie wings over which the shutter lies. The curved surface causes the shutter to flex open when moved to the open position to hold the shutter in the open position and thereby constitute the retaining means.

Preferably, the shutter has an aperture therein for allowing a tool to pass to facilitate movement of the shutter from the closed position to the open position. It is also preferred that the lingual face of the body between the wings has a notch therein to accommodate a tool passing through the aperture when the shutter is in a closed position.

According to another aspect of the present invention there is provided an pre-engaging orthodontic bracket for attaching an archwire to a tooth comprising:

a body having a lingual surface for attachment to a tooth, a pair of laterally spaced gingival tie wings and a pair of laterally spaced occlusal tie wings, said gingival and occlusal tie wings projecting from a labial surface of said body;

an archwire slot extending mesiodistally across said body and between the gingival and occlusal tie wings at opposed mesial and distal sides of said body to accommodate an archwire;

a locking shutter slidable relative to said body between an open position in which placement and removal of said archwire in said archwire slot is facilitated and a closed position in which placement and removal of said archwire in said archwire slot is inhibited; and retaining means operable upon said shutter to releasably retain said shutter in said closed position.

In one embodiment of this aspect of the present invention, it is preferred that the shutter is pivotally mounted on the body and that the retaining means is in the form of a detent constituted by mating formations on the shutter and body. In one form, the detent is constituted by at least one indentation formed on the shutter and at least one complimentary dimple formed in one of the tie wings.

In another embodiment of this aspect of the present invention, it is preferred that the retaining means is in the form of biasing means to urge the shutter to the closed position. Preferably, the shutter is slidable into slots formed in the occlusal tie wings to move the shutter to the open position, with each of the slots accommodating a spring to urge the shutter to the closed position and constitute the biasing means. It is also preferred that the orthodontic bracket includes second retaining means in the form of complimentary formations formed on the shutter and the slots to retain the shutter in the open position.

In yet another embodiment of this aspect of the present invention, it is preferred that the shutter is slidable along aligned grooves formed in the mesial and distal faces of the body through the gingival and occlusal tie wings at opposed mesial and distal ends of the body to move the shutter between the closed and open positions. In this embodiment, the shutter includes a pair of arms accommodated by the grooves and a bight bridging one end of each arm. Complimentary formations are formed on the ends of the arms and grooves to constitute the retaining means. It is also preferred that the orthodontic bracket further includes a guide extending from the bight which is accommodated in a guide channel formed in the body to guide the shutter during movement thereof between the open and closed positions.

According to still yet another aspect of the present invention there is provided an pre-engaging orthodontic bracket for attaching an archwire to a tooth comprising:

a body having a lingual surface for attachment to a tooth, a pair of laterally spaced gingival tie wings and a pair of laterally spaced occlusal tie wings, said gingival and occlusal tie wings projecting from a labial surface of said body, an archwire slot extending mesiodistally across said body and between the gingival and occlusal tie wings at opposed mesial and distal sides of said body to accommodate an archwire;

a locking shutter moveable relative to said body between an open position in which placement and removal of said archwire in said archwire slot is facilitated and a closed position in which placement and removal of said archwire in said archwire slot is inhibited; and biasing means carried by said shutter and engageable with an archwire in said archwire slot when said shutter is in said closed position, said biasing means resiliently urging said archwire into said archwire slot to provide a continuous corrective force thereon.

The present invention provides advantages in that the orthodontic bracket provides predictability and accurate control of tooth movement while enhancing treatment progress. The orthodontic bracket is aesthetically pleasing due to its symmetrical design and provides for easier hygiene than prior art orthodontic brackets. Also, the shutter is retained in a closed condition to inhibit labial movement of the archwire.

BRIEF DESCRIPTION OF THE DRAWINGS

Preferred embodiments of the present invention will now be described more fully with reference to the accompanying drawings, in which:

FIG. 6 is a front elevational view of yet another alternative embodiment of a pre-engaging twin orthodontic bracket in accordance with the present invention;

FIG. 7 is a cross-sectional view of FIG. 6 taken along line 7—7;

FIG. 17b is a side elevational view of the orthodontic bracket shown in FIG. 17a;

FIG. 59 is a front elevational view of yet another embodiment of an orthodontic bracket in accordance with the present invention similar to that shown in FIGS. 32 to 36;

FIG. 60a is a side elevational view of the orthodontic bracket of FIG. 59;

FIG. 61 is a side elevational view of a shutter forming part of the orthodontic bracket of FIG. 59;

FIG. 62 is a front elevational view of the shutter of FIG. 61;

DETAILED DESCRIPTION OF THE PREFERRED EMBODIMENT

Figure 1:
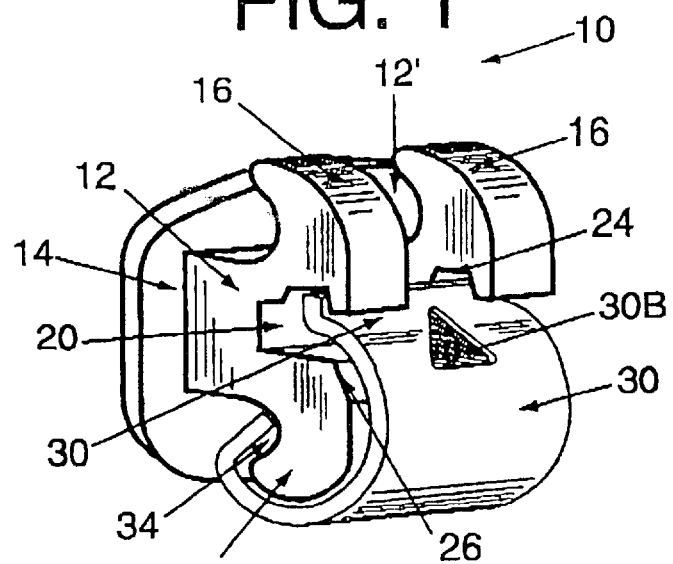
FIG. 1 is a perspective view of a pre-engaging twin orthodontic bracket in accordance with the present invention.

Referring now to FIGS. 1 and 2, a pre-engaging twin orthodontic bracket is shown and is generally indicated to by reference numeral 10. As can be seen, orthodontic bracket 10 includes a body 12 and a lingual mounting pad 14 attached to the body. The mounting pad 14 has a lingual surface to be attached to a tooth. A pair of laterally spaced gingival tie wings 16 and a pair of laterally spaced occlusal tie wings 18 extend from a labial surface of the body 12. The gingival tie wings 16 and the occlusal tie wings 18 curve lingually. An archwire slot 20 extends mesiodistally across the body and between the gingival and occlusal tie wings at opposed mesial and distal sides of the body and opens labially to receive an archwire 22. The archwire slot 20 is interrupted in the interwing region 12' of the body. A V-shaped deflection notch is formed in the gingival wall of the archwire slot 20 at its mesial and distal ends extends to define mesial and distal bevelled deflection surfaces 24 above the archwire slot. Resting grooves 26 are formed in the labial surface of the wings 15 below the archwire slot 20.

Figure 2A:
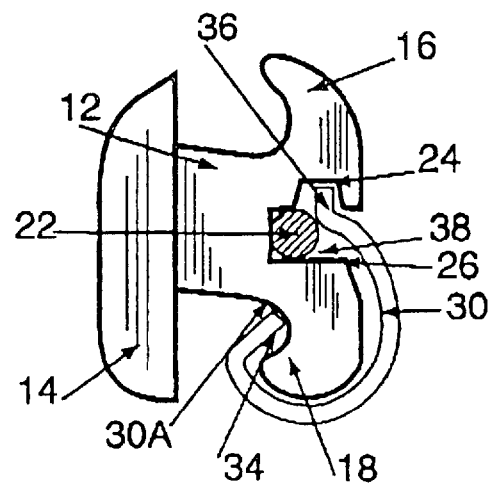
FIG. 2a is a side elevational view of the orthodontic bracket of FIG. 1.
Figure 2B:
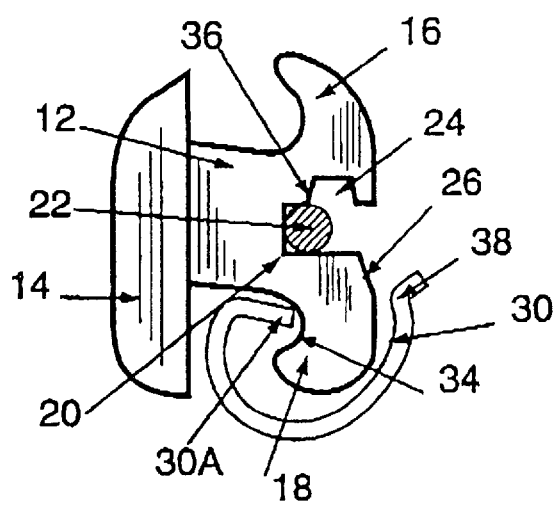
FIG. 2b is a side elevational view of the orthodontic bracket of FIG. 1 in an open position.

A shutter 30 formed of resilient stainless steel is pivotally mounted on the occlusal tie wings 18 and is movable between a closed position where access to the archwire slot 20 is inhibited and an open position where access to the archwire slot is permitted (see FIGS. 2a and 2b). One end 30a of the shutter 30 is accommodated in undercuts 34 defined by the occlusal tie wings 18. The end 30a of the shutter 30 accommodated by the undercuts 34 generally resembles an open "D" and is configured to remain in the undercuts 34 throughout movement of the shutter between the open and closed positions. As the shutter 30 moves between the open and closed positions, the end 30a of the shutter translates within the undercuts 34. An aperture 30b is formed in the shutter 30 to accommodate a tool to facilitate opening of the shutter.

The shutter 30 curves labially and gingivally around the occlusal tie wings 18 and then curves lingually towards the archwire slot 20. When the shutter 30 is in the closed position and the archwire applies a labially directed force to the shutter 30, the gingival end 36 of the shutter 30 contacts the deflection surfaces 24 to inhibit the shutter from being accidentally removed from the archwire slot 20. At the same time, the lingual surface 38 of the shutter 30 contacts the archwire 22 to urge it continuously into the archwire slot 20. When the shutter 30 is pivoted and translated to remove it from the archwire slot 20, the gingival end 36 can be accommodated by the resting grooves 26 to hold the shutter in the open position although this is not necessary as shown by the dotted line in FIG. 2b. This is due to the fact that as the compressed shutter 30 is opened, it flexes over the occlusal tie wings 18 as the shutter pivots and translates in the occlusal undercuts 34 to maintain the shutter open. The shutter 30 can be closed using a finger by simply pushing on the shutter until the gingival end 36 of the shutter enters the archwire slot 20 with the lingual surface 38 in contact with the archwire 22. The shutter 30 can be opened by inserting a one or two prong ligature director into the aperture 30b and applying an occlusally directed force on the shutter in the interwing region 12' of the body 12.

Figure 3A:
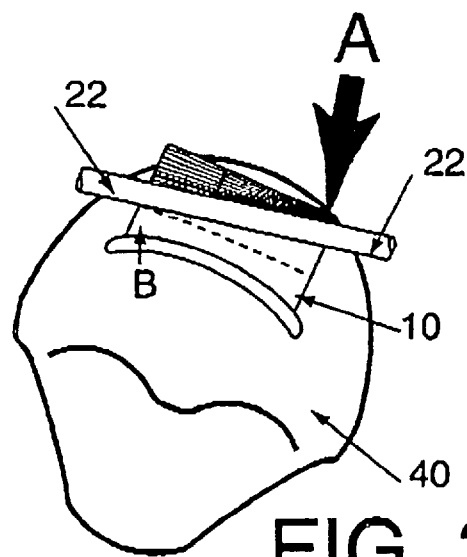
FIGS. 3a and 3b are occlusal views of an incisor section to which the orthodontic bracket of FIG. 1 of the present invention is attached, showing low deflection moment during movement of the tooth.
Figure 3B:
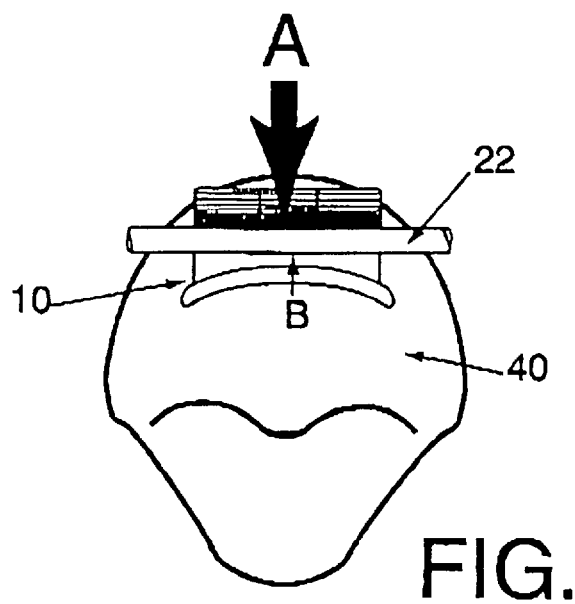

The design of the shutter 30 is such that a rectangular archwire 22 is seated to apply torque to the archwire slot 20 depending on the rectangular cross-sectional shape of the archwire 22. The continuous active seating or biasing of the archwire 22 by the shutter 30 provides for accurate tooth movement. Referring now to FIGS. 3a and 3b, a tooth 40 with an orthodontic bracket 10 on it is shown. In FIG. 3a, the tooth 40 is shown in an original "rotated" position while in FIG. 3b, the tooth is shown in a final "straight" position. The designations A and B in FIGS. 3a and 3b denote coupled sets of force vectors applied by the shutter 30 on the orthodontic bracket 10 and archwire. As can be seen, the archwire 22 in FIG. 3a deflects the shutter 30 labially on the right side reducing the initial force and moment applied to the tooth 40 until the shutter gradually seats itself into the archwire slot 20 as shown in FIG. 3b with less patient discomfort.

Figure 4:
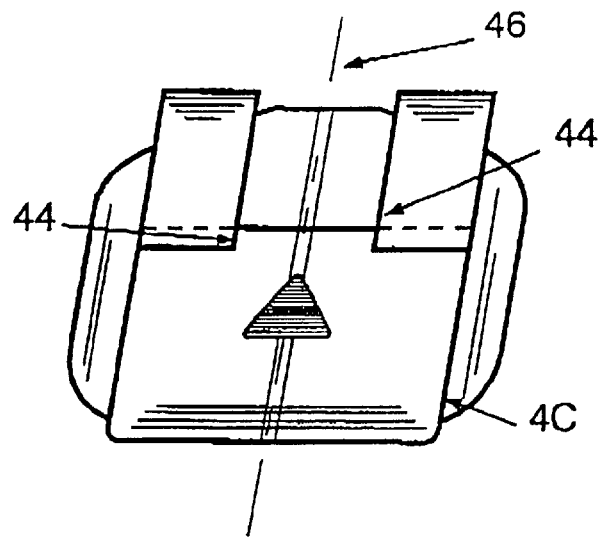
FIG. 4 is a front elevational view of an orthodontic bracket of the type shown in FIG. 1 positioned on a tooth.

Referring now to FIG. 4, an orthodontic bracket 10 is shown on a tooth 40. The occlusal edges of the orthodontic bracket 10 are preferably parallel to the incisal edges and parallel to the archwire slot. Two scribe lines 44 on the orthodontic bracket 10 delineate the long axis 46 of the tooth 40 for ideal placement of the orthodontic bracket. Also, the external lingual surface of the mounting pad 14 is angulated or biased to assist alignment and placement of the orthodontic bracket 10 against the long axis of the tooth. Larger brackets may be used for larger molars.

Figure 5:
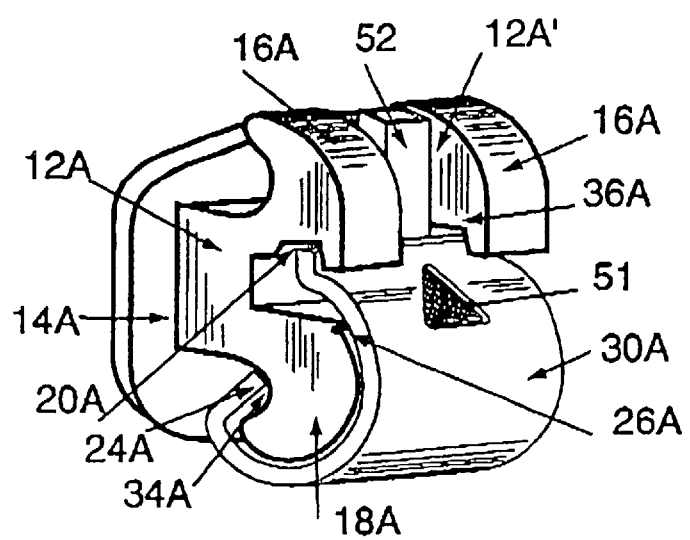
FIG. 5 is a perspective view of an alternative embodiment of a pre-engaging twin orthodontic bracket in accordance with the present invention.
Figure 8:
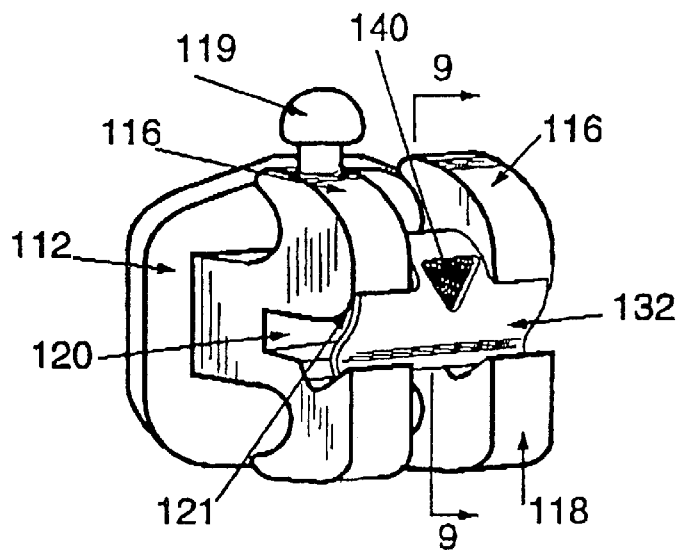
FIG. 8 is a three-quarter perspective view of the orthodontic bracket of FIG. 6.

Referring now to FIG. 5, an alternative embodiment of an orthodontic bracket is shown and is generally indicated to by reference numeral 10a. In this embodiment, like reference numerals will be used to indicate like components of the first embodiment with an "a" added for clarity. As can be seen, the shutter 24a is received in undercuts 34a defined by the occlusal tie wings 18a. The shutter 30a has an aperture 51 formed in it to receive a tool and facilitate pivoting of the shutter from the closed to open positions using a tool. A hollow vertical slot 52 is provided on the body 12a in the interwing region 12a'. The hollow slot 52 allows the orthodontic bracket 10a to provide for more tooth inclination, torque control and overcorrection than prior art orthodontic brackets.

Referring now to FIGS. 6 to 10, yet another embodiment of a pre-engaging twin orthodontic bracket is shown and is generally indicated to by reference numeral 110. As can be seen, orthodontic bracket 110 includes a body 112 and a lingual mounting pad 114 attached to the body. The mounting pad 114 has a lingual surface to be attached to a tooth. A pair of laterally spaced gingival tie wings 116 and a pair of laterally spaced occlusal tie wings 118 extend from a labial surface of the body 112. The gingival tie wings 116 and the occlusal tie wings 118 curve lingually. A horizontal crossbar 117 extends across the interwing region 112' of the body 112 and interconnects the occlusal tie wings 118. A ball hook 119 extends from one of the gingival tie wings 116.

The gingival surface 115 of the body in the interwing region 112' between the gingival tie wings 116 is convex and is generally semi-elliptical. The labial surface of the body in the interwing region 112 has a notch 150 formed in it. The gingival tie wings 116 are bevelled as indicated by reference numeral 121. An archwire slot 120 extends mesiodistally across the body 112 and between the gingival and occlusal tie wings located at opposed mesial and distal sides of the body and opens labially to receive an archwire 122. The occlusal wall of the archwire slot 120 is continuous and is constituted by the occlusal tie wings 118 and the crossbar 117. The occlusal wall of the archwire slot 120 has a notch formed in it to define two deflection surfaces 124 and 126 respectively. Deflection surface 124 is constituted by a labial bevel while deflection surface 126 is constituted by a lingual bevel.

Figure 10:
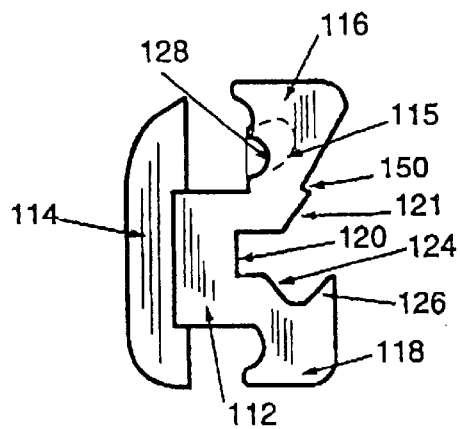
FIG. 10 is an enlarged cross-sectional view of a position of the orthodontic bracket of FIG. 8 with the pivot pin omitted.

Looking at FIGS. 7 and 10, it can be seen that a curved groove 128 is formed in the gingival tie wings 116 and interwing region 112' of the body and extends mesiodistally. The groove 128 is spaced above the gingival surface of the body 112 and accommodates a pivot pin 130. The pivot pin 130 is bonded to the gingival tie wings 116 by suitable means such as brazing, soldering, welding or the like. A shutter 132 resembling an inverted "T" in front elevation is pivotally mounted on the pivot pin 130 in the interwing region 112' and is movable between a closed position where access to the archwire slot 120 is inhibited and an open position where access to the archwire slot 120 is permitted.

Figure 11A:
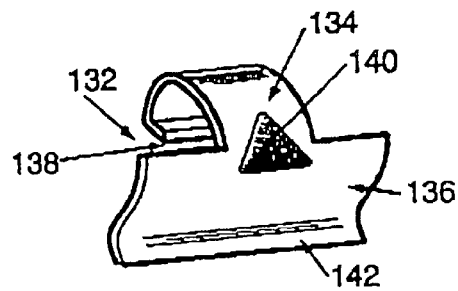
FIG. 11a and 11b are perspective and front elevational views respectively of a shutter forming part of the orthodontic bracket of FIG. 6.
Figure 11B:
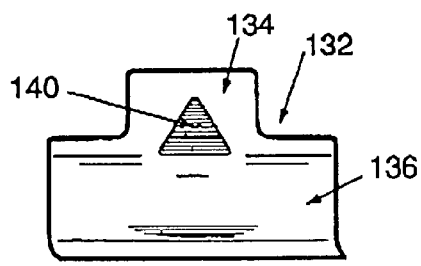

Referring now to FIGS. 11a and 11b, the shutter 132 is better illustrated. As can be seen, the shutter 132 includes a lingually curved upright stem 134 and a transverse arm 136 at the occlusal end of the stem. The edges of the shutter are curved at the intersection between the stem 134 and transverse arm 136 to strengthen the shutter. The stem 134 curves over itself at its gingival end and terminates in an open D-shaped cup 138 which partially surrounds the pivot pin 130 and is accommodated in an undercut 39 formed in the interwing region 112' occlusally of the pivot pin to secure the shutter to the orthodontic bracket 110. A generally triangular aperture 140 is formed in the stem 134 to receive a tool to facilitate pivoting of the shutter 132 from the closed position to the open position. The occlusal portion of the transverse arm 136 of the shutter is generally convex when viewed in profile and is dimensioned to be accommodated in the archwire slot 120. The occlusal edge 142 of the transverse arm 136 is slightly concave.

The archwire slot 120 is designed to accommodate circular cross-section or rectangular cross-section archwires 122. When the archwire 122 is positioned in the archwire slot and the shutter is closed, the lingual surface of the shutter 132 contacts the archwire to urge it continuously against the body 112 (see FIG. 9a). The deflection surface 126 inhibits the shutter 132 from being accidentally removed from the archwire slot 120 when the archwire 122 applies a labially directed force to the archwire. When it is desired to open the shutter 132, a tool is inserted into the aperture 140 and is accommodated by the notch 150. The tool can then be used to pivot the shutter with sufficient force so that the occlusal edge 142 of the transverse arm 136 passes over the deflection surface 126 and so that the end of the cup 138 rotates into the undercut 139 allowing the shutter 132 to open.

Figure 9A:
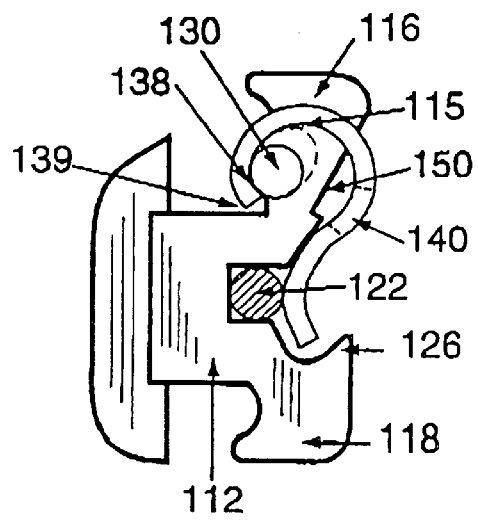
FIGS. 9a and 9b are cross-sectional views of FIG. 8 taken along line 9—9 with the shutter in closed and open positions respectively.
Figure 9B:
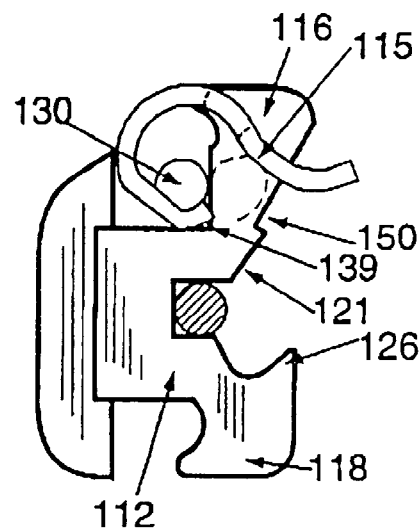

During this pivotal movement of the shutter 132, the convex interwing gingival surface 115 of the body 112 and the flexing of the initially compressed shutter over the convex surface 115 as the shutter 132 pivots around the pivot pin 130 with the end of the shutter in the notch as shown in FIG. 9b, maintains the shutter in an open condition. The undercut 139 occlusally of the pivot pin 130 provides sufficient clearance for the shutter 132 to pivot freely in a rotary fashion.

Although the shutter 132 has boon described as having a D-shaped cup 138 to surround the pivot pin 130, the shutter can curl back around itself to surround substantially the pivot pin 130 between the gingival tie wings. Also, although the pivot pin has been described as being accommodated in curved slots and bonded to the orthodontic bracket, it should be apparent to those of skill in the art that the pivot pin may be integrally formed with and extend between the gingival tie wings.

Although the gingival surface of the body in the interwing region has been described as being semi-elliptical, it should be appreciated that other surface configurations are suitable. Also, although the pivot pin has been described as being accommodated in a groove extending across the gingival tie wings and the body, the pivot pin may only extend between the gingival tie wings in the interwing region 112' making the gingival tie wings more accessible. Also, although the shutter has been shown as pivoting about a pivot pin extending between the gingival tie wings, the pivot pin may extend between the occlusal tie wings.

Referring now to FIGS. 12 to 15, yet another embodiment of an orthodontic bracket is shown and is generally indicated to by reference numeral 220. As can be seen, orthodontic bracket 220 includes a body 222 and a locking shutter 224. For illustrative purposes, the orthodontic bracket 220 is configured for a maxillary tooth but it can be appreciated that the orthodontic bracket 220 could be used on a mandibular tooth.

Body 222 includes a lingual mounting pad 226 having a lingual tooth attaching surface 228 adapted for direct attachment to a tooth or to a pad that may be attached to a tooth. A pair of laterally spaced occlusal tie wings 234 and a pair of laterally spaced gingival tie wings 236 project from a labial surface of the body 222. Each tie wing 234,236 curves lingually to define an undercut 238 for receiving a ligature. An archwire slot 240 extends mesiodistally across the body 222 and between the occlusal and gingival tie wings at opposed mesial and distal sides of the body. The archwire slot 240 accommodates an archwire 242. The archwire slot 240 has a pair of opposed surfaces 244,246 at its mesial and distal ends. Inverted V-shaped deflection notches 248 are provided in the gingival tie wings 236 above the archwire slot. The deflection notches 248 are provided to receive a gingival edge 250 of the locking shutter 224 in the closed position.

Figure 12:
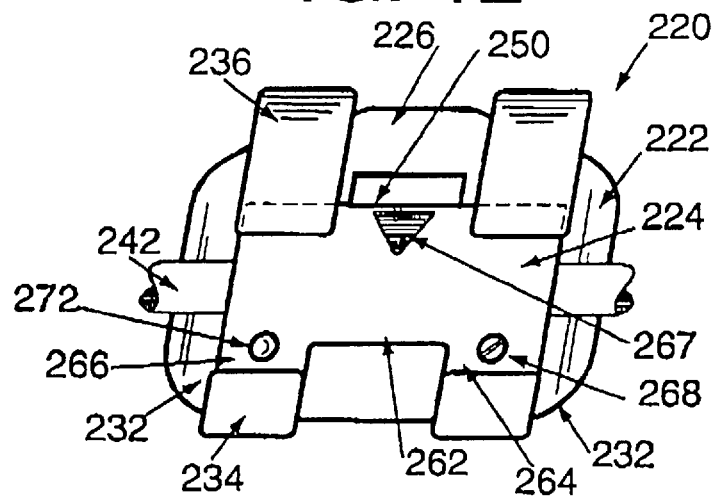
FIG. 12 is a front elevational view of an alternative embodiment of an orthodontic bracket in accordance with the present invention having a sliding shutter.
Figure 13:
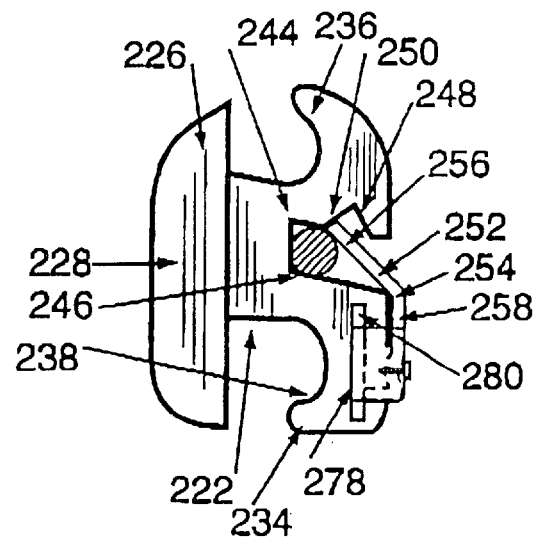
FIG. 13 is a side elevational view of the orthodontic bracket of FIG. 12.
Figure 14:
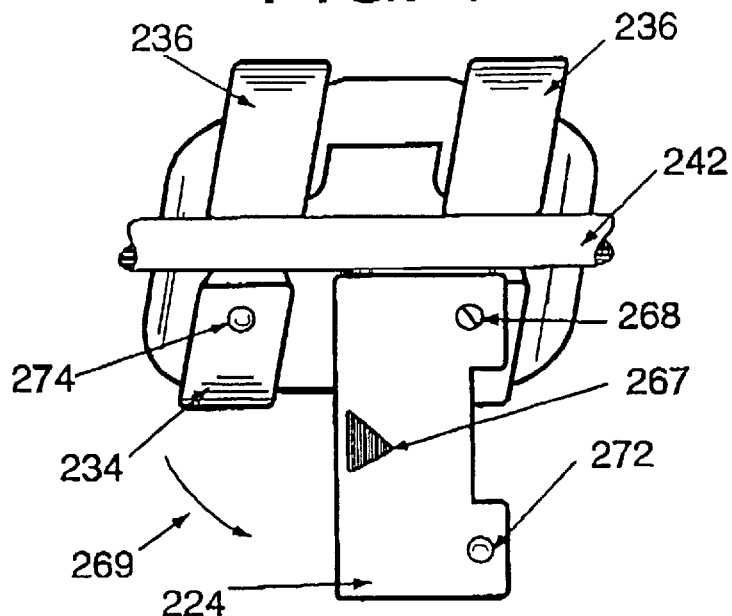
FIG. 14 is a view similar to FIG. 12 of the orthodontic bracket showing movement of the shutter to an open position.
Figure 15:
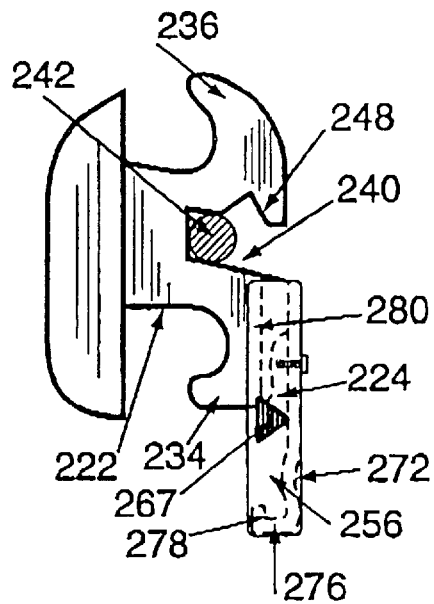
FIG. 15 is a side elevational view of the orthodontic bracket of FIG. 14 with the shutter in the open position.

The locking shutter 224 extends between the occlusal and gingival tie wings at opposed mesial and distal sides of the body 222 and across the archwire slot 240. The locking shutter 224 has a body 252 which is cranked as indicated at 254 to provide a pair of relatively inclined portions 256,258. Occlusal edge 260 of the shutter body 252 is provided with a recess 262 (as seen in FIGS. 12 and 14) so as to define a pair of downwardly projecting arms 264,266 that overlie respective ones of the occlusal tie wings 234 when the shutter 224 is in a closed position. An aperture 267 is centrally positioned on the shutter 224 to accommodate a tool to facilitate movement of the locking shutter.

The locking shutter 224 is retained on the orthodontic bracket 220 by means of an off-center pivot pin 258 that passes through an aperture (not shown) formed in the arm 264 and is secured to the occlusal tie wing 234. The shutter 224 is thus able to slide in a generally occlusal-gingival plane about the pin 268 as indicated by arrow 269 in FIG. 14.

An indentation 272 is formed in the arm 266 and a corresponding dimple 274 formed in the underlying occlusal tie wing 234. Arm 266 includes a buccally-extending return 276 that passes around the distal side of the occlusal tie wing 234 and has a retaining plate 278 that is received within a slot 280 formed in the side of the occlusal tie wing 234.

The indentation 272 cooperates with the dimple 274 to form a detent which inhibits pivotal movement of the shutter 224 about the pivot pin 268 and retains the locking shutter 224 in the closed position. The retaining plate 278 cooperates with the slot 280 and the shutter cooperates with the deflection notches 248 to inhibit labial movement of the locking shutter when in the closed position and an archwire applies a labially directed force to the shutter so that the locking shutter 224 retains the archwire 242 within the archwire slot 240.

To open the locking shutter 224, it is simply necessary to overcome the detent provided by the indentation 272 and dimple 274 and rotate the locking shutter 224 about the pivot pin 268. Access to the archwire slot 240 is thus obtained. Similarly, to close the locking shutter 224, it is simply necessary to pivot the locking shutter about the pivot pin 268 so that the gingival edge 250 engages the deflection notches 248 and the indentation 272 engages the dimple 274. The locking shutter 224 is thus held securely and cooperates with the archwire 242 to apply the requisite forces to the archwire within the archwire slot.

An alternative embodiment of an orthodontic bracket is shown in FIGS. 16a to 17b and is generally indicated to by reference numeral 220a. In this embodiment, like components of the previous embodiment will be identified with like reference numerals, with the suffix "a" added for clarity.

As can be seen, the locking shutter 224a is pivotally secured to a boss 290 that extends between the gingival tie wings 236a by way of centrally positioned pivot pin 268a. One edge 292 of the locking shutter 224a is arcuate giving the shutter 224a a generally semi-circular appearance. Deflection notches 248a are formed in the occlusal tie wings 234a adjacent the archwire slot 240a. It will be noted that the labial surfaces of the occlusal tie wings 234a are labially protrusive so that the arcuate edge 292 of the locking shutter 224a is aligned with the deflection notches 248a.

Figure 16A:
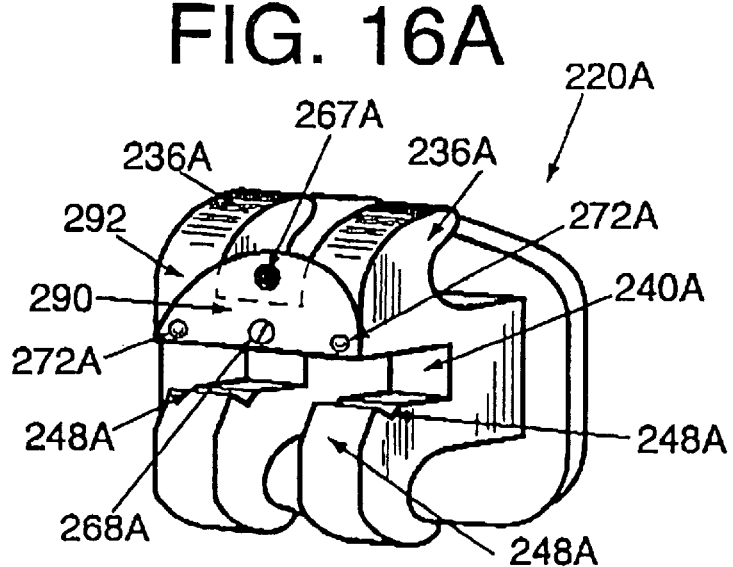
FIG. 16a is a perspective view of another alternative embodiment of an orthodontic bracket in accordance with the present invention having a sliding shutter shown in an open position.
Figure 16B:
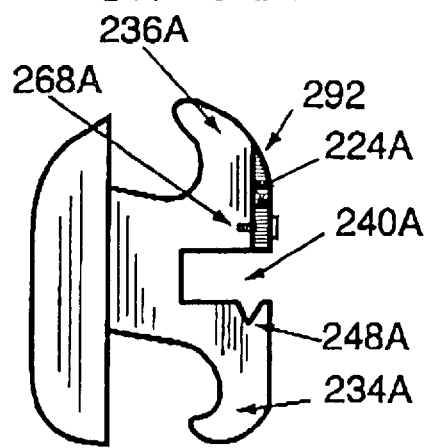
FIG. 16b is a side elevational view of the orthodontic bracket shown in FIG. 16b.
Figure 17A:
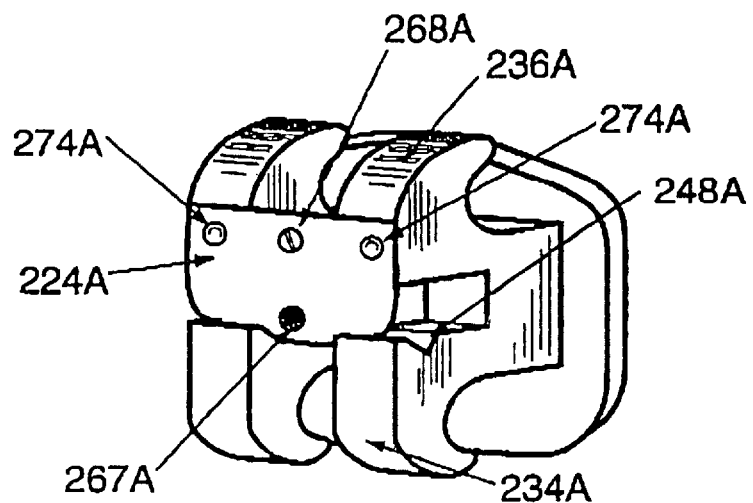
FIG. 17a is a perspective view of the orthodontic bracket of FIG. 16a showing the shutter in a closed position.
Figure 17B:
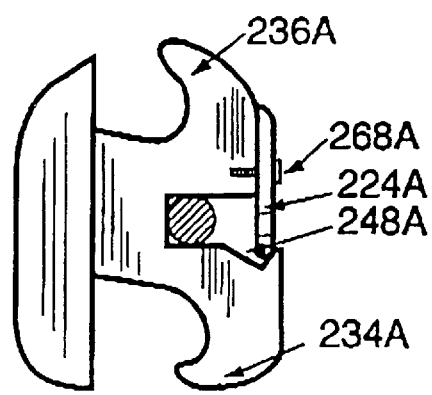

Dimples (not shown) are formed on each of the gingival tie wings 236a and corresponding indentations 272a are formed on the locking shutter 224a. The dimples and indentations 272a cooperate when the locking shutter 224a is either in the open or closed positions to retain the locking shutter in that position. An aperture 267a is provided in the shutter to receive a tool and facilitate movement of the shutter 224a. The locking shutter 224a can be pivoted about pivot pin 268a so as to bring the arcuate edge 292 into engagement with the notches 248a as shown in FIGS. 17a and 17b by overcoming the detent provided by the indentations 272a and dimples. In this position, the locking shutter 224a is effective to inhibit removal of an archwire from the archwire slot 240a. The locking shutter 224a can be readily moved to the open position by rotating the locking shutter about the pivot pin 268a to allow access to the archwire slot 240a as shown in FIG. 16a.

Figure 18:
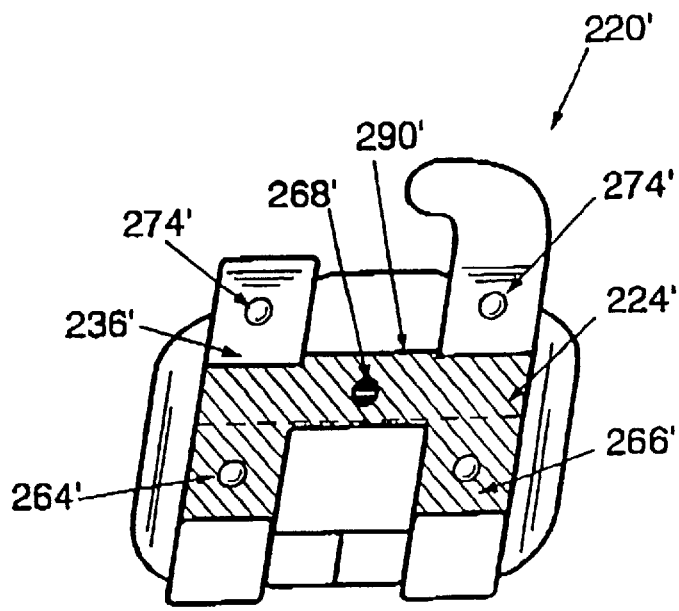
FIG. 18 is a front elevational view of an alternative embodiment of an orthodontic bracket in accordance with the present invention.
Figure 19:
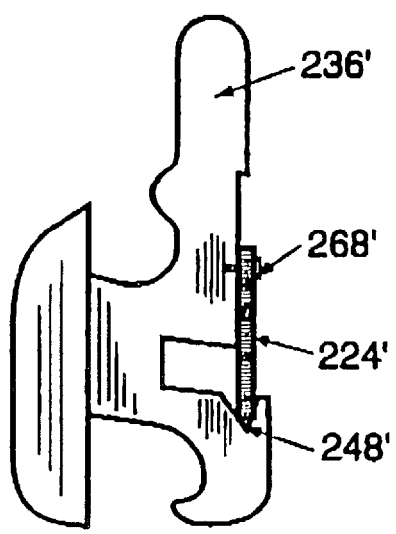
FIG. 19 is a side elevational view of the orthodontic bracket of FIG. 18.
Figure 20:
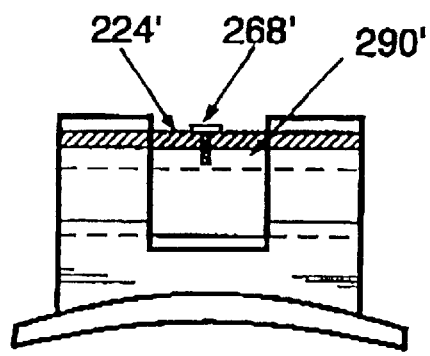
FIG. 20 is a top plan view of the orthodontic bracket of FIG. 18.
Figure 21:
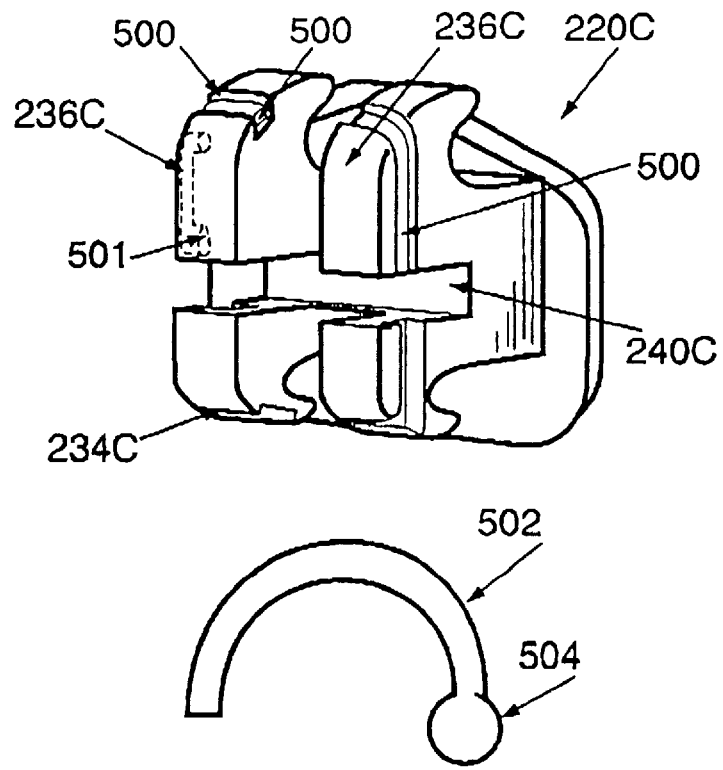
FIG. 21 is a partially exploded three quarter perspective view of a still yet another embodiment of an orthodontic bracket in accordance with the present invention.

Another alternative arrangement of an orthodontic bracket 220' is shown in FIGS. 18 to 20. In this embodiment, like reference numerals will be used to indicate like components of the embodiment of FIGS. 12 to 15 with the suffix "'" added for clarity. In this embodiment, the locking shutter 224' is relieved and is generally C-shaped to provide a pair of arms 264' and 266'. Similar to the previous embodiment, the locking shutter 224' is pivotally secured to a boss 290' extending between the gingival tie wings 236' by way of a pivot pin 268'. A dimple 274' is provided on both gingival tie wings 236'. Indentations 272' on the arms 264' and 266' co-operate with the dimples 274' with the detent formed between the indentations and dimples maintaining the locking shutter 224' in the open position. The notches 248' define deflection surfaces to inhibit labial movement of the shutter 224' and its removal from the archwire slot 240' when the shutter 224' is in the closed position and an archwire applies a labially directed force to the shutter. In order to move the shutter from the open to closed position, it is necessary to overcome the detent provided by the indentations 272' and the dimples 274' and pivot the shutter 224' about the pivot pin 268'.

In embodiments of the orthodontic brackets illustrated in FIGS. 12 to 20, it will be observed that movement of the locking shutter between open and closed positions is obtained by simple rotation of the locking shutter about the pivot pin so that the locking shutter remains captive to the body but at the same time is securely held in the closed and/or open positions by the action of the detent formed between the indentations and dimples.

A further embodiment of an orthodontic bracket is shown in FIGS. 21 to 24, in which like reference numerals will be used to denote like components of the embodiment of FIGS. 12 to 15 with a suffix 'c' added for clarity. As can be seen, a circular track 500 is formed on the mesial, distal, occlusal and gingival sides of the orthodontic bracket 220c. The circular track 500 passes through the occlusal and gingival tie wings 234c and 236c respectively to intersect the archwire slot 240c. Bores 501 are formed in the circular tracks 500 in the mesial and distal sides of the gingival tie wings 236c slightly above the archwire slot 240c. The archwire slot 240c is offset occlusally so that the gingival tie wings 236c are longer than the occlusal tie wings 234c.

The track 500 receives a shutter in the form of a part circular clip 502 having a circular protrusion 504 at one end. The clip 502 is slidable in the track 500 but provide a friction grip against the track to inhibit unintentional movement. The circular protrusion 504 is accommodated by one of the bores 501 to hold the clip 502 in either the closed or open positions.

Figure 22:
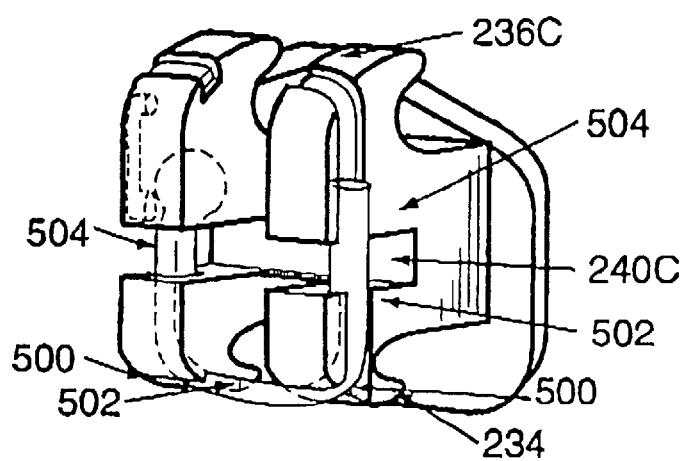
FIG. 22 is a three-quarter perspective view similar to FIG. 21 of the orthodontic bracket in a closed position.
Figure 23:
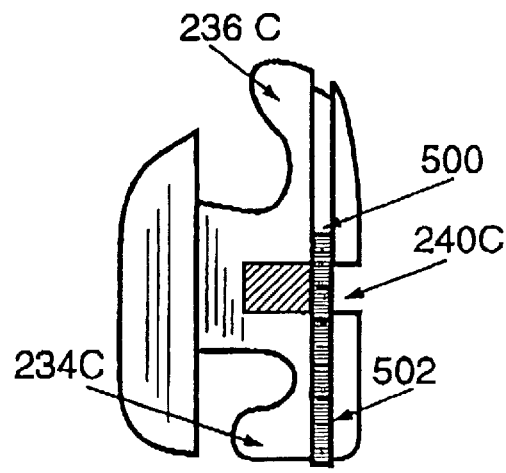
FIG. 23 is a side elevational view of the orthodontic bracket of FIG. 22 accommodating an archwire.
Figure 24:
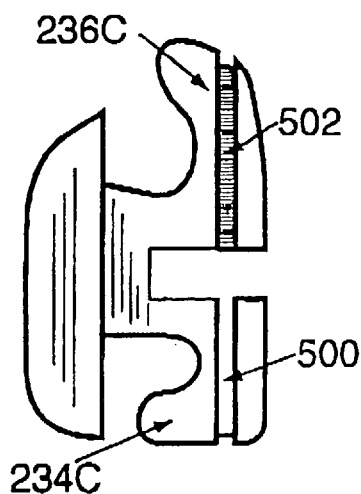
FIG. 24 is a side elevational view of the orthodontic bracket of FIG. 22 in an open position.

The clip 502 may be rotated in the track 500 between an open position in which access to the archwire slot 240c is available (see FIG. 24) and a closed position in which access is inhibited (see FIGS. 22 and 23). As can best be seen in FIG. 22, the offset of the archwire slot 240c allows the clip 502 to overlie the archwire slot 240c to retain an archwire within the archwire slot. Rotation of the clip 502 through approximately 180 degrees moves the clip to the position shown in FIG. 24 at which the archwire slot 240c is open and access to the archwire is provided. The circular protrusion 504 facilitates rotation of the clip 502 between open and closed positions, with the friction between the clip and the track 500 and the cooperating protrusion 504 and bore 501 retaining the clip 502 in the desired position.

Figure 25:
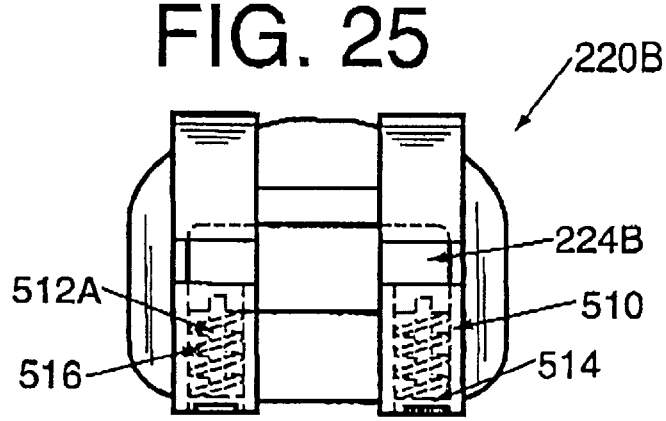
FIG. 25 is a front elevational view of a further embodiment of an orthodontic bracket in accordance with the present invention having a resiliently biased locking shutter.
Figure 26:
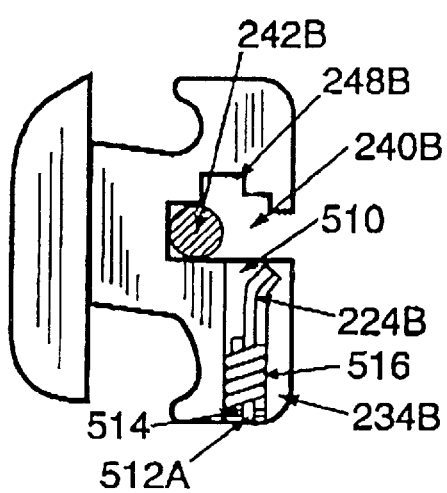
FIG. 26 is a side elevational view of the orthodontic bracket of FIG. 25 in an open position.
Figure 27:
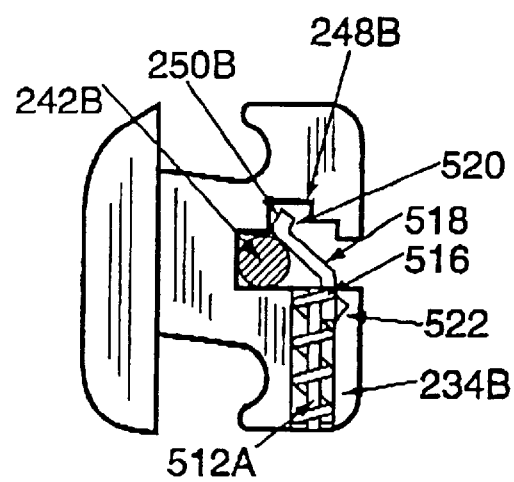
FIG. 27 is a side elevational view of the orthodontic bracket of FIG. 25 in a closed position.
Figure 28:
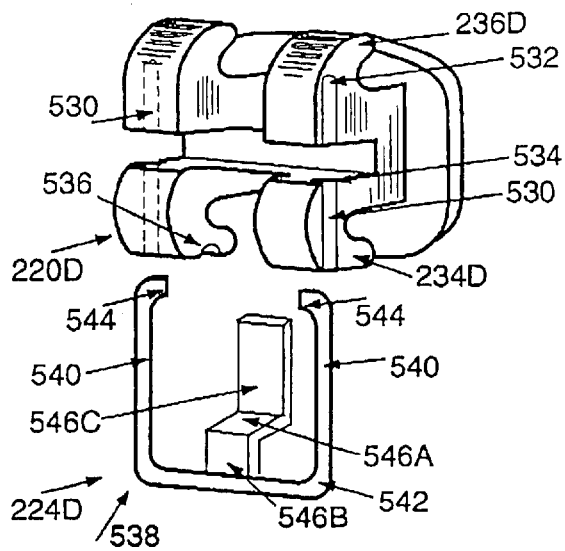
FIG. 28 is an exploded three-quarter perspective view of yet another alternative embodiment of an orthodontic bracket in accordance with the present invention.
Figure 29:
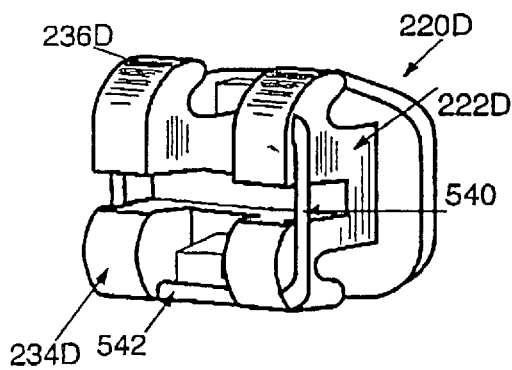
FIG. 29 is a three-quarter perspective view of the orthodontic bracket of FIG. 28 in a closed position.

A still further embodiment of an orthodontic bracket 220b is shown in FIGS. 25 to 27 in which like reference numerals will be used to denote like components of the embodiment of FIGS. 12 to 15, with a suffix "b" added for clarity. As can be seen, the shutter 224b is slidable within a slot 510 formed in each of the occlusal wings 234b. A U-shaped strap 512 is secured to the labial face of shutter 224b and extends through a guide slot 514 and a washer 515 in the base of each of the slots 510. A coil spring 516 is positioned in each slot beneath the shutter 224b and surrounds each arm 512a of the strap 512. The arms 512a are cranked slightly above the coil springs 516 toward the archwire slot 240b as indicated to by reference numeral 518. The springs 516 bias the shutter 224b to a closed position in which the gingival edge 250b of the shutter 224b engages the notches 248b.

The labial surface of the shutter 224b carries a wedge 520 that cooperates with a complementary recess 522 formed in the slots. The wedge 520 retains the shutter 224b in the open position and may be released by application of a force to the bight 512b of the strap 512 to release the shutter 224b under the action of the springs 516. The shutter 224b is thus retained in the closed position to resist labial movement of an archwire 242b in the archwire slot 240b. The spring loaded shutter 224b may also be applied in a similar manner to two single orthodontic brackets or a 3 wing orthodontic bracket.

A still further embodiment of an orthodontic bracket 220d is shown in FIGS. 28 to 31 where like reference numerals will be used to indicate like components of the embodiment illustrated in FIGS. 12 to 15 with the suffix "d" added for clarity. In this embodiment, grooves 530 are formed in the mesial and distal sides of the body 222d. Each groove 530 extends through the gingival and occlusal tie wings 236d and 234d. The grooves 530 terminate in blind bores 532 in the gingival tie wings 236d. Blind bores 534 are also formed in the grooves 530 in the occlusal tie wings 236d adjacent the archwire slot 240d (see FIG. 31). The occlusal surfaces of the occlusal tie wings 236d are undercut to provide a lateral groove 536 that extends mesiodistally between the occlusal tie wings.

A shutter 224d in the form of a generally U-shaped clip 538 is formed with a pair of outer arms 540 interconnected by a lateral bight 542. The ends of the arms 540 are formed with inwardly-directed projections 544 for receipt within the bores 532 or 534.

A support arm 546 is secured to the lateral bight 542 and is jogged to provide a horizontal arm 546a between a pair of vertical arms 546b and 546c respectively. One of the vertical arms 546c is received within a vertical slot 548 in the body 220d and maintains alignment of the clip 538 as it is moved between the open and closed positions. The slot 548 is located in the interwing region of the body 222d to provide uniform support.

Figure 30A:
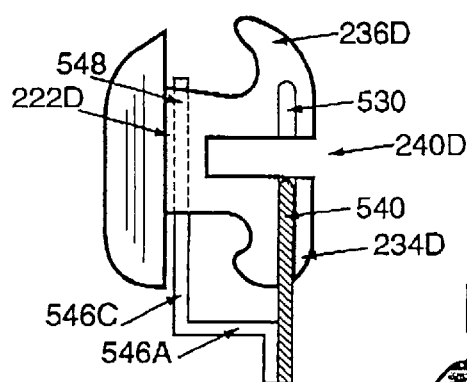
FIG. 30a is a side elevational view of the orthodontic bracket of FIG. 29 in an open position.
Figure 30B:
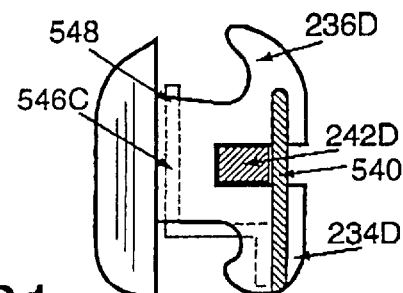
FIG. 30b is a side elevational view of the orthodontic bracket of FIG. 29 in a closed position.
Figure 31:
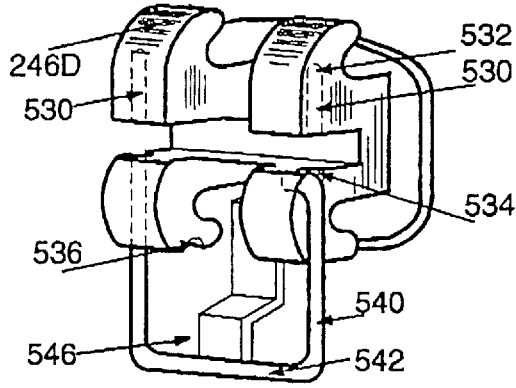
FIG. 31 is a three-quarter perspective view of the orthodontic bracket of FIG. 29 in the open position.
Figure 32:
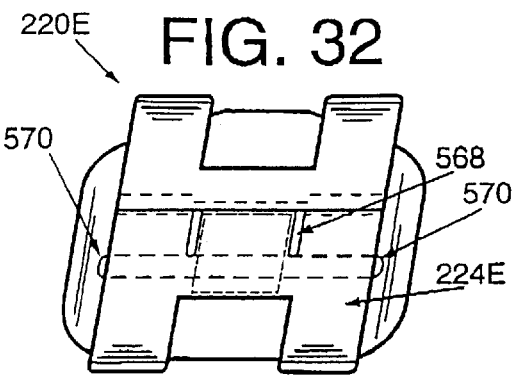
FIG. 32 is a front elevational view of yet another embodiment of an orthodontic bracket in accordance with the present invention.
Figure 33:
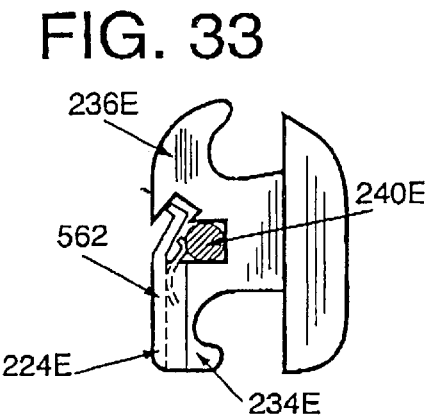
FIG. 33 is a side elevational view of the orthodontic bracket of FIG. 32.
Figure 34:
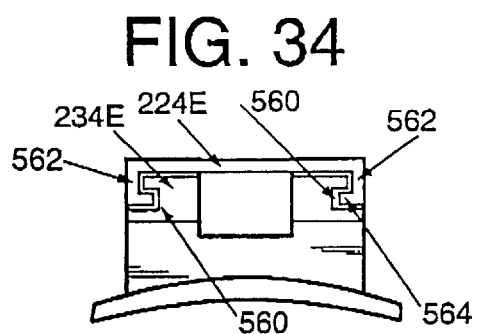
FIG. 34 is an occlusal view of the orthodontic bracket of FIG. 32.
Figure 35:
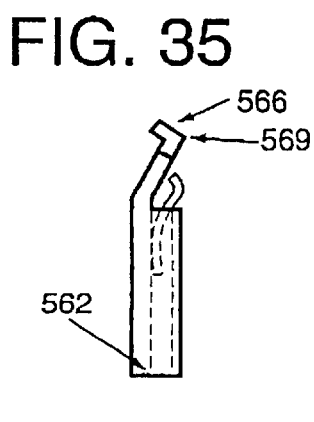
FIG. 35 is a side elevational view of a shutter forming part of the orthodontic bracket of FIG. 32.
Figure 36:
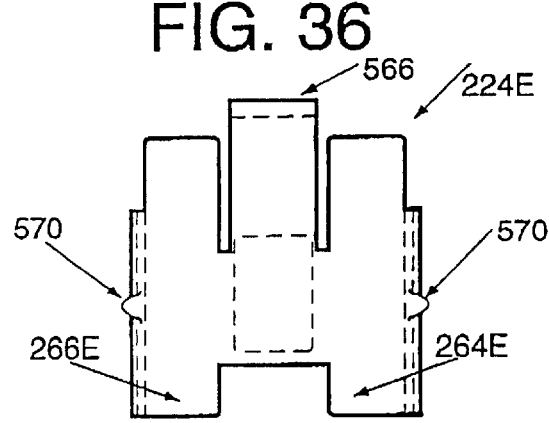
FIG. 36 is a front elevational view of the shutter of FIG. 35.

The clip 538 is assembled on the orthodontic bracket 220d so that the arms 540 are received within the respective grooves 530. The projections 544 are received within the blind bores 534 so that the archwire slot 240d is open for receipt of an archwire as shown in FIG. 30a. With the archwire 242d inserted into the archwire slot 240a as shown in FIG. 30b, the clip 538 may be advanced along the grooves 530 until the projections 544 are received within the blind bores 532. In this position, the lateral bight 542 is received within the lateral groove 536 to provide further security for the clip 538. The vertical arm 546c and slot 548 serve to guide and align the clip 538 during sliding motion to facilitate the relative movement between the clip and the orthodontic bracket 220d.

A further embodiment of an orthodontic bracket 220e is shown in FIGS. 32 to 36. In this embodiment like reference numeral will be used to denote like components of the embodiment of FIGS. 12 to 15 with a suffix "e" added for clarity. In the embodiment of FIGS. 32 to 36, grooves 560 are formed in the occlusal tie wings 234e only. The shutter 224e includes side flanges 562 that have inwardly directed protrusions 564 to engage the grooves 560. The shutter 224e has a pair of lingually angulated occlusal arms 264e and 266e and a centrally positioned gingival arm 566 defined partly by a pair of slits 568 in the shutter 224e (best seen in FIG. 36). The gingival arm 566 is recurved in a labial direction as indicated by reference numeral 569 and is resilient to engage the labial notches 248e at the mesial and distal ends of the archwire slot 240c and inhibit labial movement of shutter 224e when an archwire applies a labially directed force to the shutter. Protrusions 570 are provided on the sides of the shutter 224e to form a handle and facilitate sliding movement of the shutter 224c between the open and closed position. Again therefore, a sliding shutter is provided on the orthodontic bracket 220e to retain an archwire in the archwire slot 240e.

Figure 37:
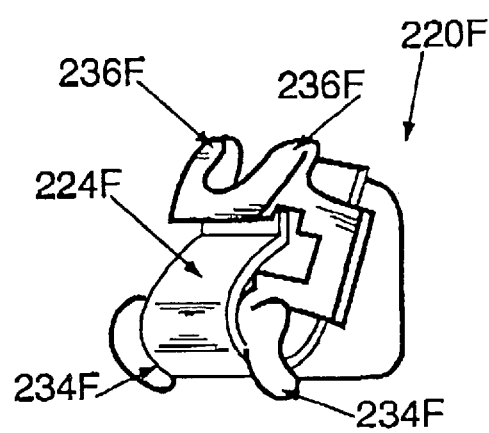
FIG. 37 is a three-quarter perspective view of still yet a further embodiment of an orthodontic bracket in accordance with the present invention.
Figure 38:
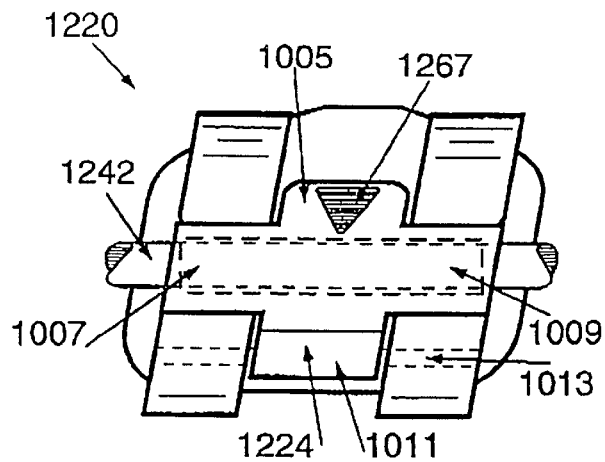
FIG. 38 is a front elevational view of yet another alternative embodiment of an orthodontic bracket in accordance with the present invention in a closed position.
Figure 40:
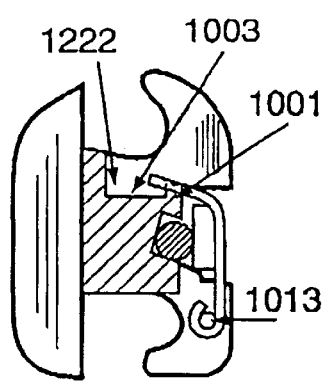
FIG. 40 is a side elevational view of the orthodontic bracket of FIG. 38 accommodating a round archwire.
Figure 39:
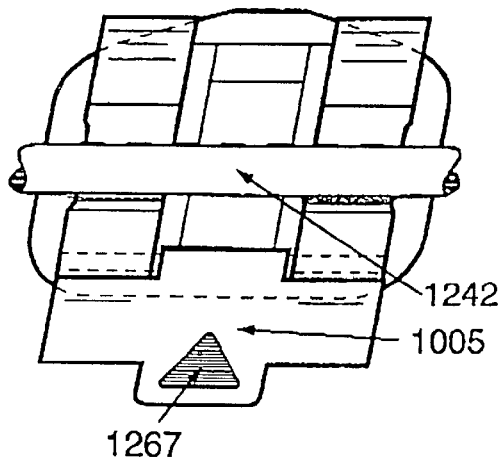
FIG. 39 is a front elevational view of the orthodontic bracket of FIG. 38 in an open position.
Figure 41:
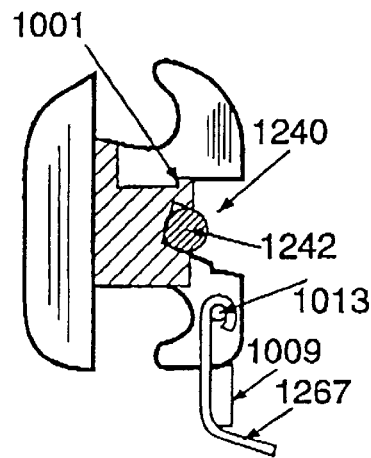
FIG. 41 is a side elevational view of the orthodontic bracket of FIG. 39 accommodating a round archwire.

In a further embodiment shown in FIG. 37, a known orthodontic bracket 220f sold under the trade name "SPEED" is shown and includes a pair of occlusal tie wings 234f below a shutter 224f and a pair of gingival tie wings above the shutter 224f to provide a twin orthodontic bracket. The gingival tie wings can be spaced further apart to make the orthodontic bracket more symmetrical.

Referring now to FIGS. 38 to 41, still yet another embodiment of an orthodontic bracket is shown. In this embodiment, like reference numerals will be used to denote like components of the embodiment of FIGS. 12 to 15 with a "1000" added for clarity. As can be seen, the orthodontic bracket 1220 is similar to one of the orthodontic brackets disclosed in Applicant's U.S. Pat. No. 5,474,445 issued on Dec. 12, 1995, the contents of which are incorporated herein by reference. In this embodiment, a projection 1001 is formed on the gingival surface 1003 of the body 1222 in the interwing region. The shutter 1224 generally resembles a cruciform and has a gingival arm 1005 with an inverted doghouse shaped aperture 1267 in it to accommodate the projection 1001 and retain the shutter 1224 in the closed position. The shape of the aperture 1267 also permits a tool to enter the aperture so that a labially directed force can be applied to the shutter 1224 using the tool to release the shutter 1224 from the projection 1001. The mesial and distal arms 1007 and 1009 respectively of the shutter 1224 curve lingually into the archwire slot 1240. The arms 1007 and 1009 are resilient and somewhat flattened when contacting a full dimension rectangular archwire 1242 accommodated in the archwire slot 1240 to apply a bias to move the archwire 1242 into the base of the archwire slot. In this way, a continuous rotation action and torque is applied to the archwire whether round or rectangular (even where that archwire is of relatively small cross-sectional dimension) to apply a continuous force to the tooth through the orthodontic bracket 1220. The occlusal arm 1011 of the shutter 1224 curves labially around a pivot pin 1013 to secure the shutter 1224 to the orthodontic bracket 1220 and to provide a shutter with a continuous smooth lingual surface.

Figure 41A:
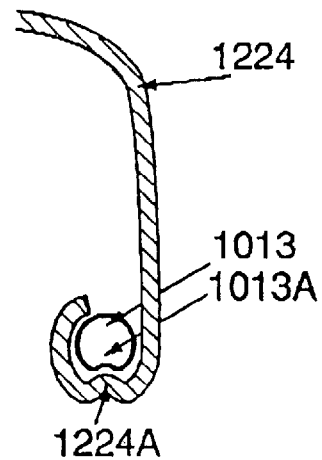
FIG. 41a is a cross-sectional view of an alternative embodiment of a pivot pin and shutter for use with the orthodontic bracket of FIG. 38.
Figure 42:
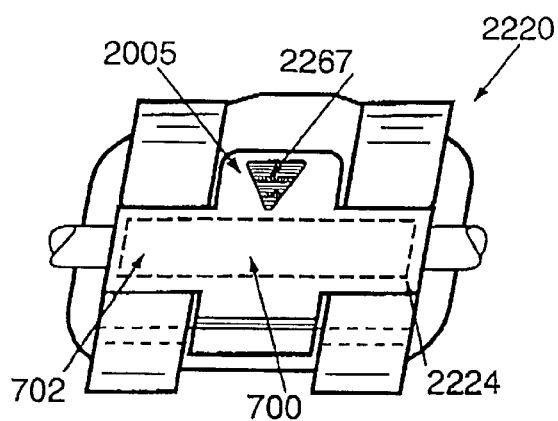
FIG. 42 is a front elevational view of yet another alternative embodiment of an orthodontic bracket in accordance with the present invention in a closed position.
Figure 44:
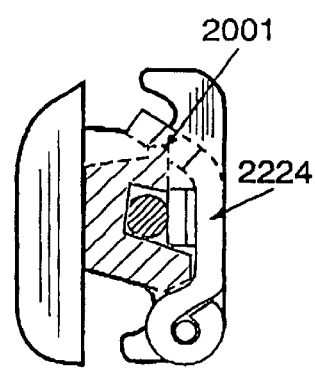
FIG. 44 is a side elevational view of the orthodontic bracket of FIG. 42 accommodating a round archwire.
Figure 43:
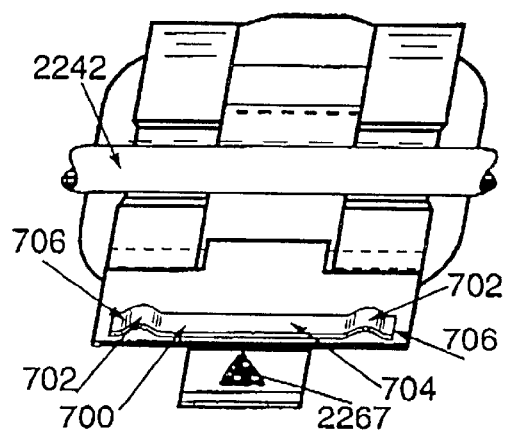
FIG. 43 is a front elevational view of the orthodontic bracket of FIG. 42 in an open position.
Figure 45:
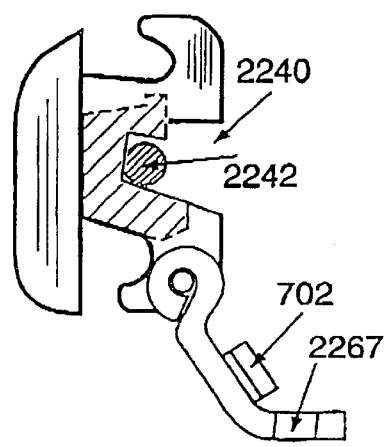
FIG. 45 is a side elevational view of the orthodontic bracket of FIG. 43 accommodating a round archwire.

FIG. 41*a* shows an alternative embodiment of the shutter and pivot pin design. In this embodiment, a dimple 1013*a* is formed in the pivot pin 1013 and an indentation 1224*a* is provided in the shutter 1224. The indentation 1224*a* and dimple 1013*a* cooperate when the shutter is in a closed position to provide further security to inhibit accidental opening of the shutter.

A similar arrangement of an orthodontic bracket 2220 to that described above is shown in FIGS. 42 to 45. In this embodiment, like reference numerals will be used to denote like components of the embodiment of FIGS. 12 to 15 with a "2000" added for clarity. As can be seen, the orthodontic bracket 2220 also has a shutter 2224 generally resembling a cruciform. The gingival arm 2005 of the shutter 2224 has a doghouse shaped aperture 2267 in it to accommodate a projection 2001 and retain the shutter 2224 in the closed position. Unlike the previous embodiment, the mesial and distal arms 2007 and 2009 on the shutter 2224 are relatively rigid. A spring member in the form of a ribbon 700 is located on the lingual surface of the shutter 2224 and extends mesiodistally. The ribbon 700 is configured to provide a pair of convex lingually extending formations 702 that are aligned with the occlusal and gingival tie wings at opposed mesial and distal sides of the body 2222 and thus bear against an archwire 2242 located in the archwire slot 2240. The central portion 704 of the ribbon 700 is secured to the shutter 2224 with the lateral extremities 706 of the ribbon being free to slide horizontally over the lingual surface of the shutter 2224 and thereby allow flexure of the formations 702. In this manner, different thicknesses of archwires 2242 can be accommodated by the orthodontic bracket 2220 while still ensuring that a continuous force is applied to the tooth through the orthodontic bracket.

Figure 45A:
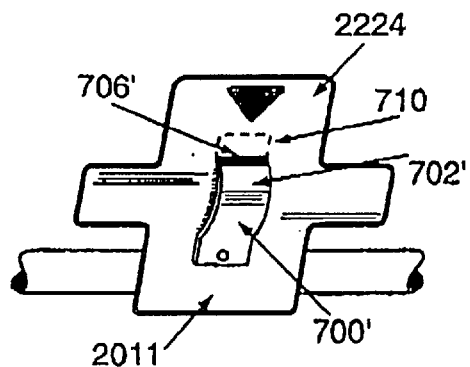
FIG. 45a is a front elevational view of an alternative embodiment of a shutter for use with the orthodontic bracket of FIG. 42.

FIG. 45*a* illustrates an alternative embodiment of a ribbon 700' for use with the orthodontic bracket 2220. In this embodiment, the ribbon 700' is secured is to the lingual surface of the occlusal arm 2011 of the shutter 2224 adjacent one of its ends and extends in a gingival-occlusal direction. The other end 706' of the ribbon 700' is free to slide relative to the lingual surface of the shutter 2224 as indicated by the dotted line 710. The tong 700' presents a convex surface 702' which enters the archwire slot 2240 when the shutter is in a closed position to bias the archwire 2242 into the archwire slot.

Figure 46:
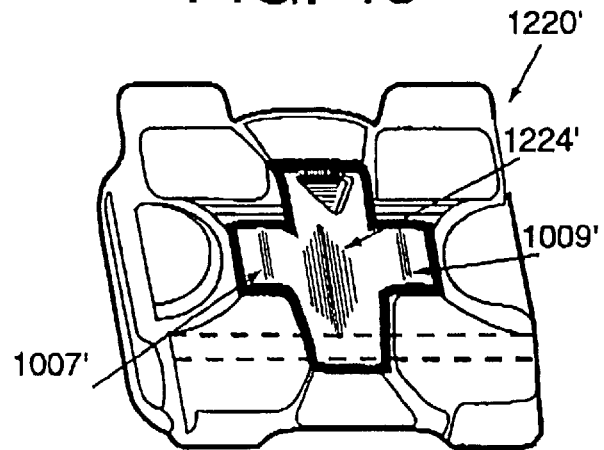
FIG. 46 is a front elevational view of yet another alternative embodiment of an orthodontic bracket in accordance with the present invention in a closed position.
Figure 47:
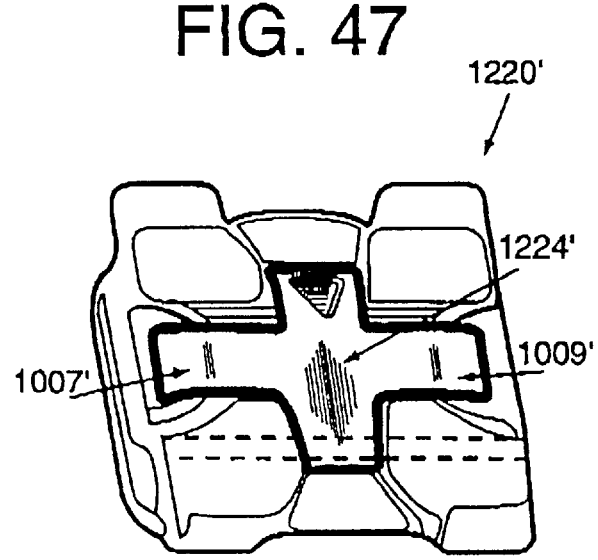
FIG. 47 is a front elevational view of yet another alternative embodiment of an orthodontic bracket in accordance with the present invention in a closed position.
Figure 48:
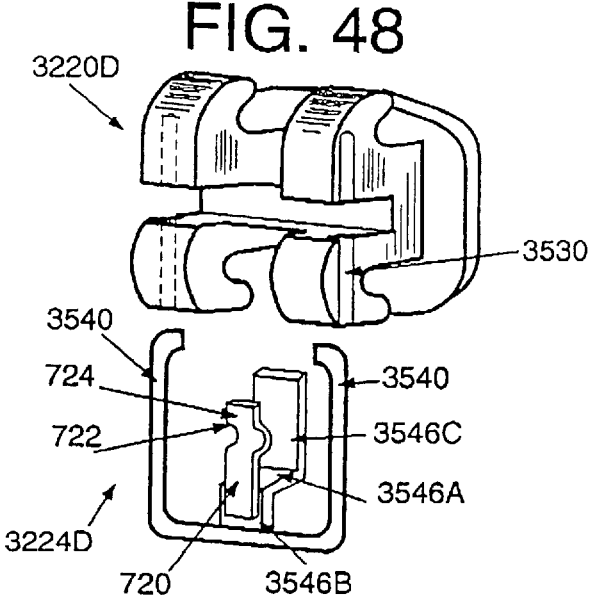
FIG. 48 is an exploded three-quarter perspective view of yet another alternative embodiment of an orthodontic bracket in accordance with the present invention similar to that shown in FIGS. 28 to 31.

FIGS. 46 and 47 illustrate alternative embodiments of orthodontic brackets 1220' similar to that illustrate in FIGS. 38 to 41. In these embodiments, like reference numerals will be used to indicate like components of the embodiment of FIGS. 38 to 41 with a "'" added for clarity. In the embodiment of FIG. 46, the shutter 1224' has short mesial and distal arms 1007' and 1009' which curve lingually into the archwire slot 1240' to apply a bias to an archwire 1242' accommodated by the archwire slot 1240'. In the embodiment of FIG. 47, the shutter 1224' has longer mesial and distal arms 1007' and 1009' which curve lingually into the archwire slot 1240' to apply a bias to an archwire 1242' accommodated by the archwire slot 1240'.

Referring now to FIGS. 48 to 52, still yet another embodiment of an orthodontic bracket 3220*d* is shown similar to that shown in FIGS. 28 to 31. In this embodiment, like reference numerals will be used to denote like components of the embodiment of FIGS. 28 to 31 with a "3000" added for clarity. As can be seen, the orthodontic bracket 3220*d* can be modified to provide a continuous seating action bias to an archwire accommodated in the archwire slot. In this arrangement, a spring member in the form of a resilient shim 720 is attached to the vertical arm 3546*b* of the support arm 3546. The shim 720 thus projects gingivally from the labial edge of the horizontal arm 3546*a* so as to be spaced from the lingual vertical arm 3546*c*. The shim 720 has a jog directed lingually toward the archwire slot 3240*d* and presents a generally convex surface 722 towards the archwire slot 3240*d*. The gingival edge 724 of the shim 720 recurves labially.

Figure 49:
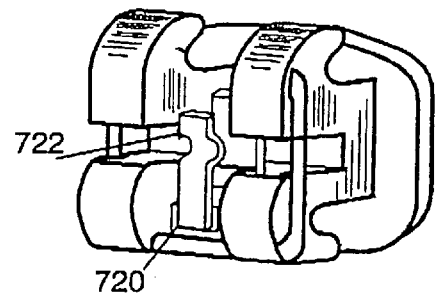
FIG. 49 is a three-quarter perspective view of the orthodontic bracket of FIG. 48 in a closed position.
Figure 50:
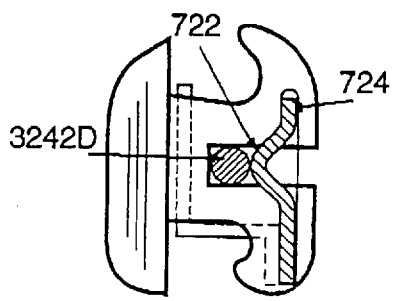
FIG. 50 is a side elevational view of the orthodontic bracket of FIG. 49 in an open position.
Figure 51:
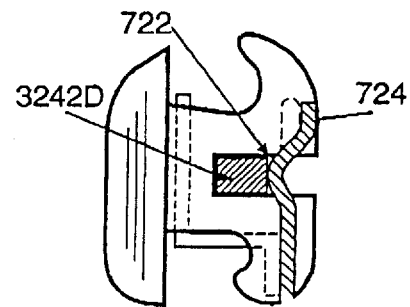
FIG. 51 is a side elevational view of the orthodontic bracket of FIG. 49 in a closed position.
Figure 52:
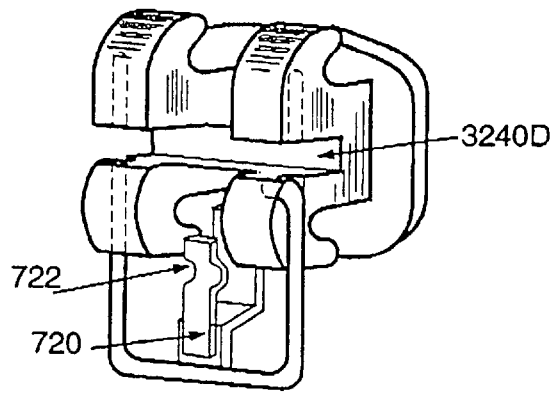
FIG. 52 is a three-quarter perspective view of the orthodontic bracket of FIG. 49 in the open position.

As the arms 3540 slide within the slots 3530 to the move the clip 3538 to a closed position as shown in FIG. 49, the convex surface 722 of the shim 720 engages the archwire 3242*d* and provides a continuous biasing action against the archwire (best seen in FIG. 50). As may be seen in FIG. 51, the resilience of the shim 720 allows the orthodontic bracket 3220*d* to accommodate different sizes and configurations of archwire 3242*d* while maintaining a continuous action against the archwire.

Figure 53:
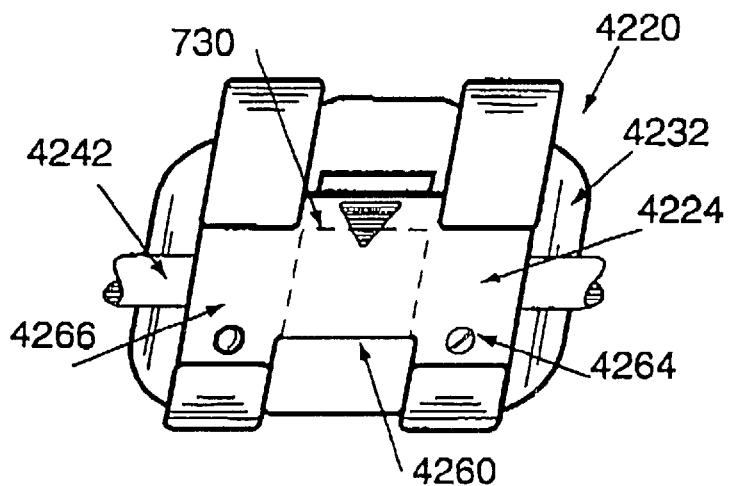
FIG. 53 is a front elevational view of an alternative embodiment of an orthodontic bracket in accordance with the present invention having a sliding shutter similar to that shown in FIGS. 12 to 15.
Figure 55:
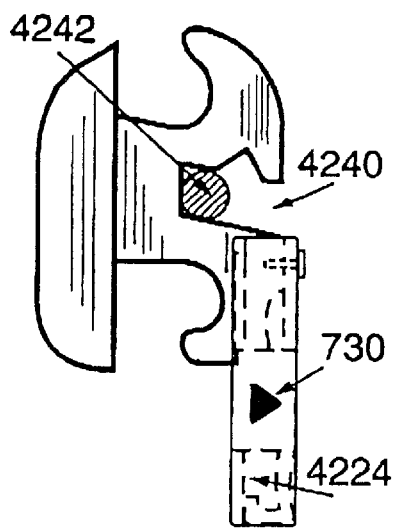
FIG. 55 is a side elevational view of the orthodontic bracket of FIG. 53 with the shutter in the open position.
Figure 54:
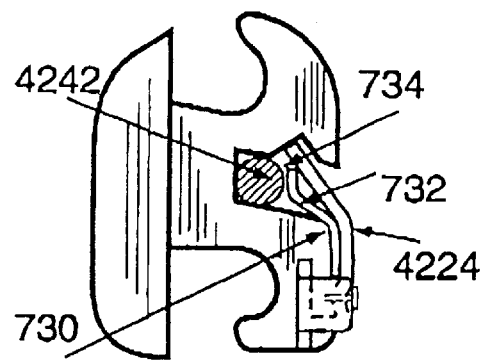
FIG. 54 is a side elevational view of the orthodontic bracket of FIG. 53.

Referring now to FIGS. 53 to 55, still yet another embodiment of an orthodontic bracket 4220 is shown similar to that shown in FIGS. 12 to 15. In this embodiment, like reference numerals will be used to denote like components of the embodiment of FIGS. 12 to 15 with a "4000" added for clarity. As can be seen, the orthodontic bracket 4220 can be modified to provide a continuous bias to an archwire accommodated in the archwire slot. In this embodiment, a spring member in the form of a resilient shim 730 is secured to the lingual surface of the shutter 4224 adjacent the interwing region of the body 4220. The shim 730 is integrally formed with the shutter 4224 and is folded lingually about the occlusal edge 4260 of the shutter between the arms 4264 and 4266 respectively. The shim 730 is curved lingually to present a generally convex surface 732 spaced from the shutter 4224 and its end 734 recurved to form a smooth lip engaged with the lingual face of the shutter 4224. The end 734 of the shim 730 is free to slide relative to the shutter 4224 when the convex surface 731 is flattened due to contact with an archwire 4242 in the archwire slot 4240. The shim 730 is thus able to continuously exert a corrective force upon different configurations of archwires 4242 within the archwire slot 4240 when the shutter 4224 is in the closed position.

Figure 56:
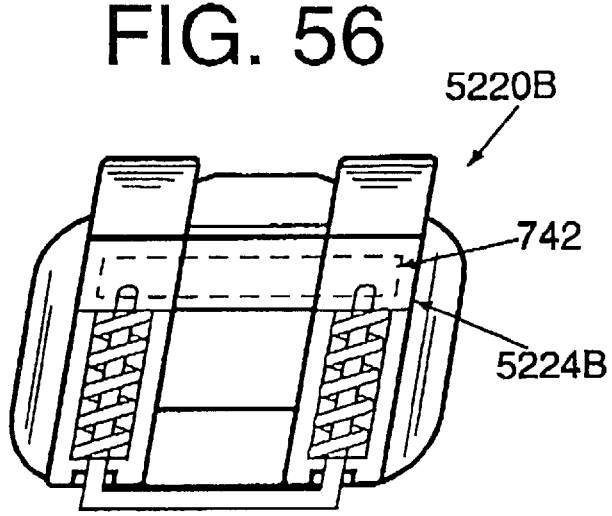
FIG. 56 is a front elevational view of a further embodiment of an orthodontic bracket in accordance with the present invention having a resiliently biased locking shutter similar to that shown in FIGS. 25 to 27.
Figure 57:
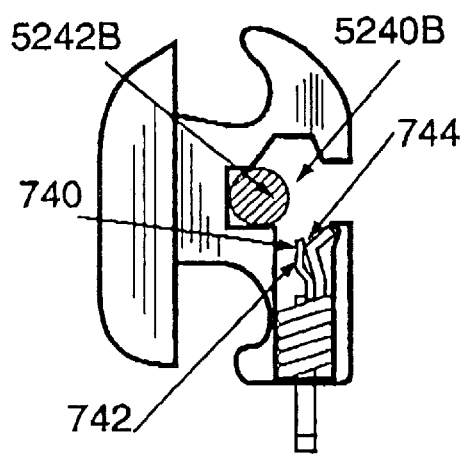
FIG. 57 is a side elevational view of the orthodontic bracket of FIG. 56 in an open position.
Figure 58:
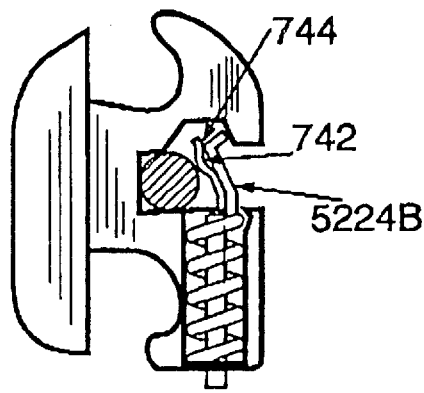
FIG. 58 is a side elevational view of the orthodontic bracket of FIG. 56 in a closed position.
Figure 60B:
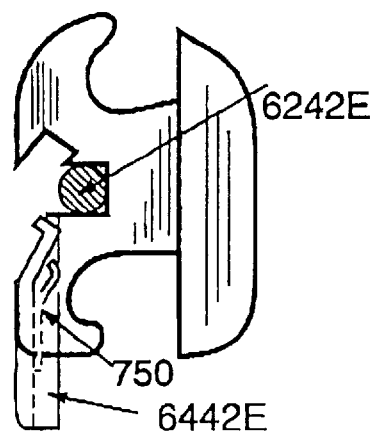
FIG. 60b is a side elevational view of the orthodontic bracket of FIG. 59 in an open position.
Figure 63:
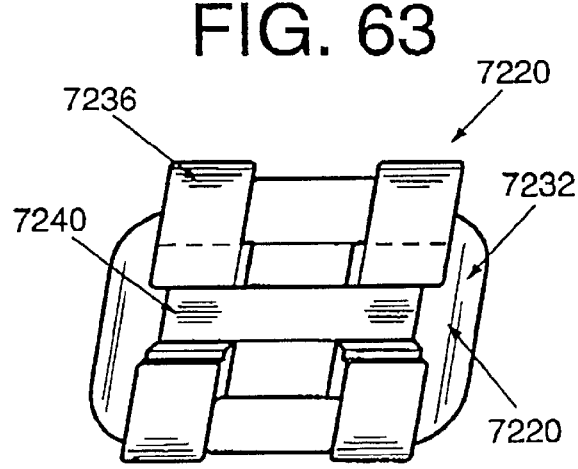
FIG. 63 is a front elevational view of still a further embodiment of an orthodontic bracket in accordance with the present invention with the shutter removed.
Figure 64:
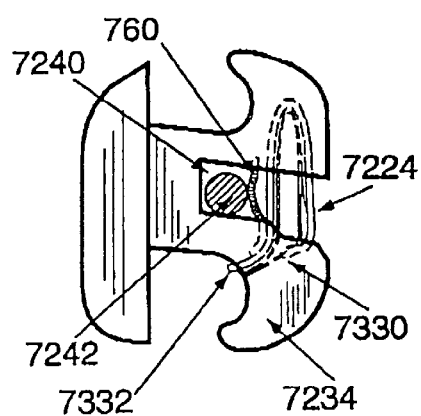
FIG. 64 is a side elevational view of the orthodontic bracket of FIG. 63 with the shutter installed.
Figure 65:
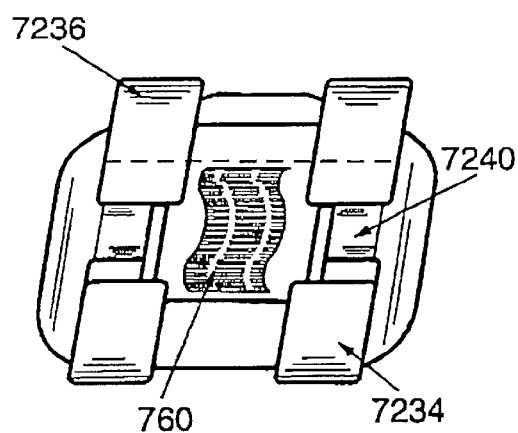
FIG. 65 is a front elevational view of the orthodontic bracket of FIG. 63 with the shutter installed.
Figure 66:
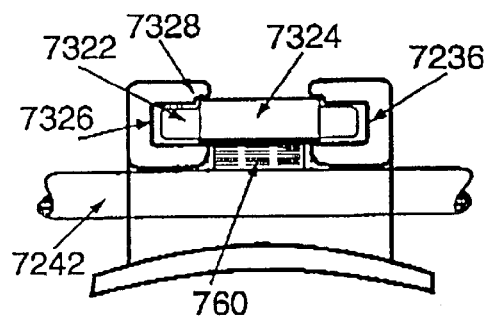
FIG. 66 is a top plan view of the orthodontic bracket of FIG. 65.

Referring now to FIGS. 56 to 58, still yet another embodiment of an orthodontic bracket 5220*b* is shown similar to that shown in FIGS. 25 to 27. In this embodiment, like reference numerals will be used to denote like components of the embodiment of FIGS. 25 to 27 with a "5000" added for clarity. As can be seen, the orthodontic bracket 5220*b* can be modified to provide a continuous bias to an archwire accommodated in the archwire slot. In the arrangement shown, a spring member in the form of a resilient shim 740 is formed on the lingual face of the shutter 5224*b* in the archwire slot 5240*b*. The shim 740 is formed with a convex lingual surface 742 that engages an archwire 5242*b* when the shutter 5224*b* is in the closed position. The shim 740 is secured to the shutter 5224*b* adjacent its occlusal end only and therefore, the gingival end 744 of the shim 740 is free to slide relative to the shutter 5224*b*. In this manner, the shim 740 may flex to accommodate different sizes and shapes of archwires 5242*b* accommodated in the archwire slot 5240*b* to provide a continuous action on the archwire wire.

Referring now to FIGS. 59 to 62, still yet another embodiment of an orthodontic bracket 6220*e* is shown similar to that shown in FIGS. 32 to 36. In this embodiment, like reference numerals will be used to denote like components of the embodiment of FIGS. 32 to 36 with a "6000" added for clarity. As can be seen, the orthodontic bracket 6220e can be modified to provide a continuous bias to an archwire accommodated in the archwire slot. In the arrangement shown, a spring member in the form of a shim 750 is secured to the lingual surface of the shutter 6224c and presents a convex surface 752 toward the archwire slot 6240e to engage an archwire 6242b in the same manner as described above to provide a continuous action on the archwire wire. The gingival edge 754 of the shim is free to slide relative to the lingual surface of the shutter 6224e.

A continuously acting orthodontic bracket may also be provided with self-locking labial brackets such as those shown in U.S. Pat. No. 5,094,614 to Wildman, the contents of which are incorporated herein by reference. As shown in FIGS. 63 to 71, the orthodontic bracket 7220 has a pair of wings 7242 with an archwire slot 7240 to receive an archwire 7242.

Figure 67:
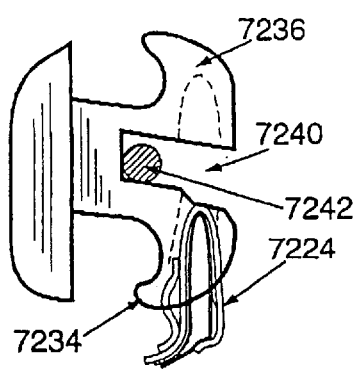
FIG. 67 is a side elevational view of the orthodontic bracket of FIG. 63, similar to FIG. 64, with the shutter in an open position.
Figure 69:
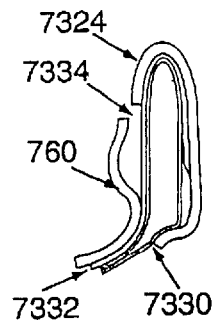
FIG. 69 is a side elevational view of an alternative embodiment of a shutter for use with the orthodontic bracket of FIG. 63.
Figure 68:
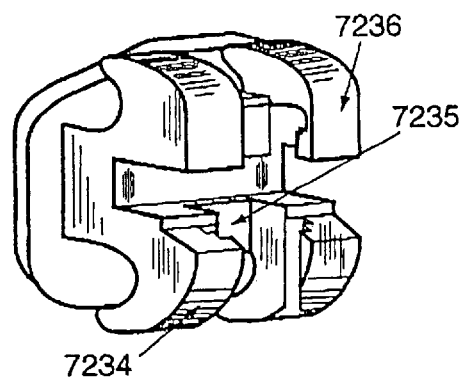
FIG. 68 is a three-quarter perspective view of the orthodontic bracket of FIG. 63.

A shutter 7224 is located between the gingival and occlusal tie wings located at opposed mesial and distal sides of the body 7222 and includes a central body portion 7322 encompassed by a locking spring 7324. The mesial and distal edges of the shutter body 7322 are received within grooves 7326 so that the shutter 7224 may slide between open and closed positions. The grooves 7326 have undercuts 7328 that terminate at steps 7330 in the occlusal and gingival tie wings 7234 and 7236 respectively. The steps 7330 receive one end of a spring 7324. The opposite ends are formed as an occlusal tail. A spring member in the form of a resilient shim 760 is secured to the tail 7332 so as to be spaced from the retaining spring 7324. A lingual step 7235 accommodates the shim 760 from a lingual aspect. The shim 760 thus engages an archwire 7242 in the archwire slot 7240 when the shutter 7224 is in the closed position in a resilient manner to provide a continuous biasing action against the archwire as shown in FIG. 6b. The step 7330 retains the shutter 7224 in the closed position with the resilient shim 760 biased against the archwire 7242. As shown in FIG. 67, the shim 760 may be secured to the tail 7332 as a separate structure. Alternatively, as shown in FIG. 69, the shim 760 may be formed on the tail 7332 of a liner layer 7334 that encompasses the body 7322. The spring 7324 extends over the upper edge of the body 7322 and terminates above the upper edge of the shim 760. The shim 760 is thus free to flex to accommodate different sizes and dispositions of archwires while providing a continuous action on the archwire.

Figure 70:
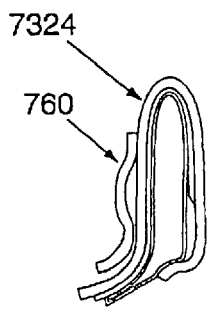
FIG. 70 is a side elevational view of a further alternative embodiment of a shutter for use with the orthodontic bracket of FIG. 63.
Figure 71:
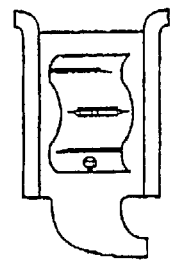
FIG. 71 is a rear elevational view of the shutter of FIG. 70.

Similarly, as shown in FIG. 70, the shim 760 may be secured at its upper edge to the spring 7324 with the lower edge free of the tong to slide relative to the shutter upon flexure of the shim 760.

Figure 72:
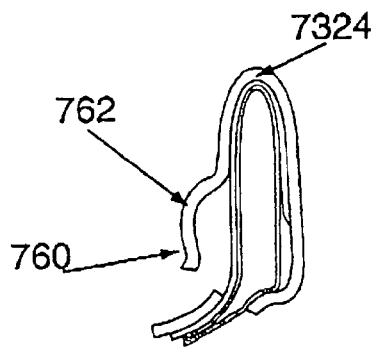
FIG. 72 is a side elevational view of a still further embodiment of a shutter for use with the orthodontic bracket of FIG. 63.
Figure 73:
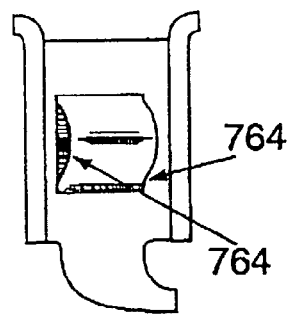
FIG. 73 is a rear elevational view of the shutter of FIG. 72.
Figure 74:
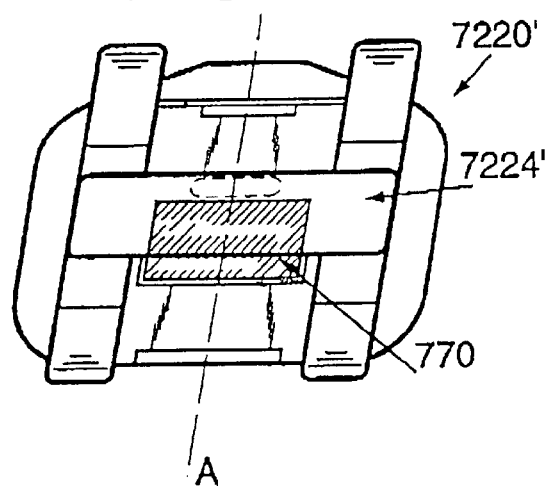
FIG. 74 is a front elevational view of yet another alternative embodiment of an orthodontic bracket in accordance with the present invention.
Figure 75:
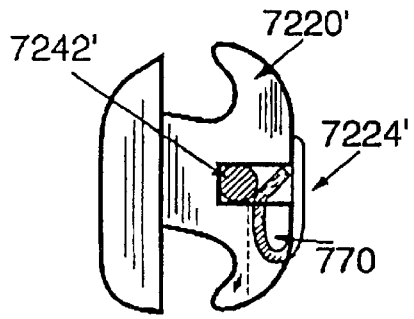
FIG. 75 is a side elevational view of the orthodontic bracket of FIG. 74 in a closed position.
Figure 76:
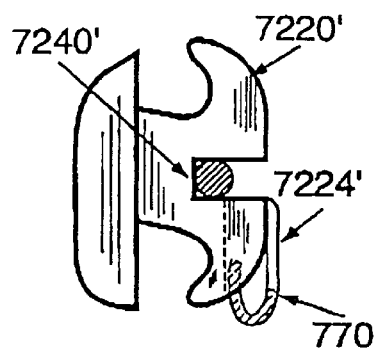
FIG. 76 is a side elevational view of the orthodontic bracket of FIG. 75 in an open position.
Figure 77:
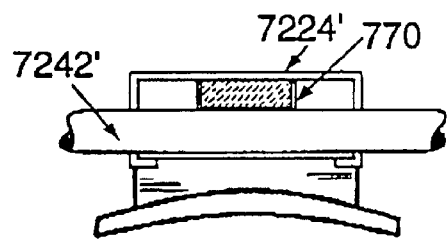
FIG. 77 is a cross-sectional view of FIG. 76.
Figure 78:
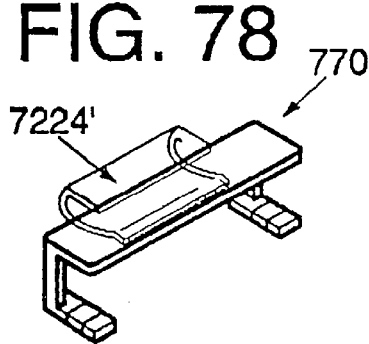
FIG. 78 is a perspective view of a shutter used in the orthodontic bracket of FIG. 74.
Figure 79:
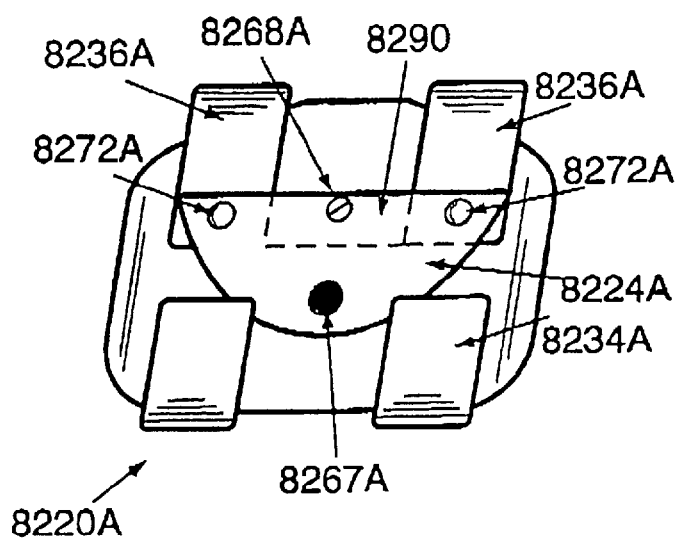
FIG. 79 is a front elevational view of yet another alternative embodiment of an orthodontic bracket in accordance with the present invention.
Figure 80:
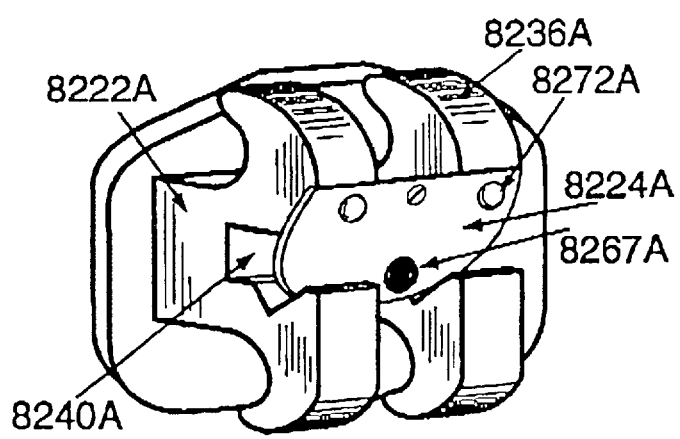
FIG. 80 is a perspective view of the orthodontic bracket of FIG. 79.

An alternative arrangement for the shim 760 is shown in FIGS. 72 and 73. In this embodiment, the resilient shim 760 is defined in the lingual aspect of the outer layer of the spring 7324. Three sides of the shim 760 are defined by slots 764 cut into the lingual aspect of the outer layer of the spring to define the periphery of the shim 760. The resultant shim defines an inwardly convex surface 762 that resiliently engages the archwire. Naturally, such a shim 760 may be formed integrally with the springs 7324 to facilitate manufacture.

A further modification of an existing orthodontic bracket 7220' is shown in FIGS. 74 to 78 in which the orthodontic bracket known as the Damon bracket and shown in U.S. Pat. No. 5,439,378, the contents of which are incorporated herein by reference, is modified to provide a spring member in the form of a resilient shim 770 on the lingual surface of the shutter 7224'. Shutter 7224' may be extended occlusally to accommodate the shim 770 which in this embodiment is formed by folding a continuous extension of the shutter 7224' back upon itself. The shim 770 presents a convex surface 772 which enters the archwire slot 7240' when the shutter 7224' is in a closed position. One end 744 of shim 770 is free to slide relative to the shutter 7224'. In this manner, the shim 770 may flex to accommodate different sizes and shapes of archwires 7242' accommodated in the archwire slot 7240' to provide a continuous action on the archwire.

As those of skill in the art will appreciate, in the embodiments illustrated in FIGS. 38 to 78, the spring member may be formed as a separate member and attached to the shutter adjacent either its gingival or occlusal ends in a manner so that it extends into the archwire slot to bias the archwire. Alternatively, the spring member may be integrally formed with the shutter by a folding portion of the shutter about an edge. If the spring member is to be integrally formed with the shutter, a continuous extension of the shutter is typically folded about either a gingival or occlusal edge of the shutter and is configured so that it extends into the archwire slot to bias the archwire.

Referring now to FIGS. 79 to 82, still yet another embodiment of an orthodontic bracket 8220 is shown similar to that shown in FIGS. 16a to 17a. In this embodiment, like reference numerals will be used to denote like components of the embodiment of FIGS. 16a to 17b with a "8000" added for clarity. As can be seen, the resilient locking shutter 8224a is pivotally secured to a boss 8290 that extends between the gingival tie wings 8236a by way of a centrally located pivot pin 8268a. The boss 8290 is located on a lingually bevelled labial surface of the body 822a. Thus, the shutter 8224a is inclined. One edge 8292 of the locking shutter 8224a is arcuate to give the shutter a generally semi-circular appearance. Deflection notches 8248a are formed in the archwire slot 8240a adjacent the occlusal tie wings 8234a.

Figure 81:
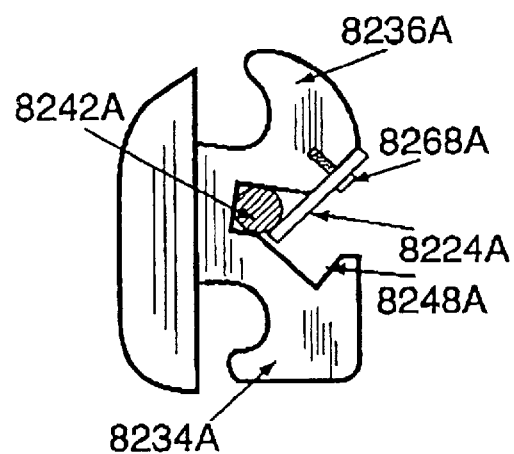
FIG. 81 is a side elevational view of the orthodontic bracket of FIG. 79.
Figure 82:
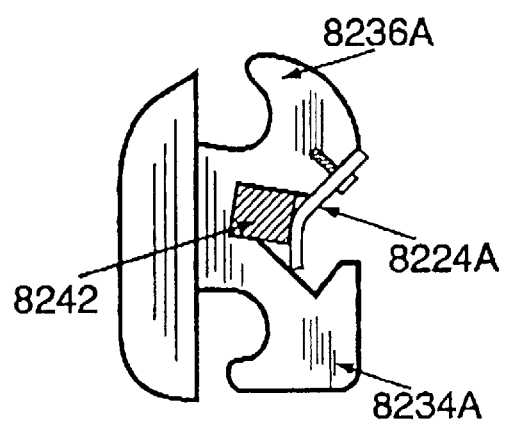
FIG. 82 is a side elevational view of the orthodontic bracket of FIG. 79 accommodating a larger archwire.

Dimples (not shown) are formed on each of the gingival tie wings 8236a and corresponding indentations 8272a are formed on the locking shutter 8224a. The dimples and indentations 8272a cooperate when the locking shutter 8224a is either in the open or closed positions to retain the locking shutter in that position. An aperture 8267a is provided in the shutter 8224a to receive a tool and facilitate movement of the shutter 8224a. The locking shutter 8224a can be pivoted about pivot pin 8268a so as to bring the shutter 8224a into engagement with the archwire 8242a in the archwire slot 8240a as shown in FIG. 81 by overcoming the detent provided by the indentations 8272a and dimples. In this position, the locking shutter 8224a is effective to inhibit removal of an archwire 8242 from the archwire slot 8240a and provides a continuous action on the archwire. The locking shutter 8224a can be readily moved to the open position by rotating the locking shutter about the pivot pin 8268a to allow access to the archwire slot 8240a. As can be seen in FIG. 82, when a larger archwire 8242 is accommodated by the archwire slot 8240a, the shutter 8224a flexes to accommodate the archwire yet provide a continuous action on the archwire. The deflection notches 8248a and the angulated orientation of the shutter 8224a inhibit the shutter 8224a from moving labially out of the archwire slot 8240a.

Another embodiment of an orthodontic bracket 9220 utilizing an alternative shutter structure is shown in FIGS. 83 to 87. In this embodiment, like reference numerals will be used to denote like components of the embodiment of FIGS.

12 to 15 with a suffix '9000' added for clarity. As shown in FIGS. 83 to 87, the shutter 9224 is pivotal and is formed from a wire 9001 bent into a generally cruciform outline. The wire 9001 has opposite ends that are turned over to provide oppositely-directed tails 9003 and 9005. The tails 9003, 9005 extend parallel to a common axis but are offset from one another.

Each of the tails 9003, 9005 is received in a respective bore 9007 formed in each of the occlusal tie wings 9234. The tails 9003, 9005 are free to rotate within the respective bores to permit pivotal movement of the shutter 9224.

The wire 9001 defines a pair of oppositely-directed arms 9009, 9011 which extend across the archwire slot 9240. A horizontal recess 9013 is formed in each of the gingival tie wings 9236 adjacent the archwire slot 9240 to provide an abutment surface to limit pivotal movement of the shutter 9224 towards the archwire slot 9240.

Figure 84:
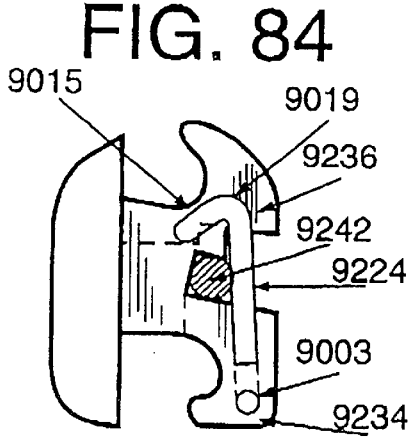
FIG. 84 is a side elevational view of the orthodontic bracket of FIG. 83 in a closed position and accommodating an archwire.
Figure 85:
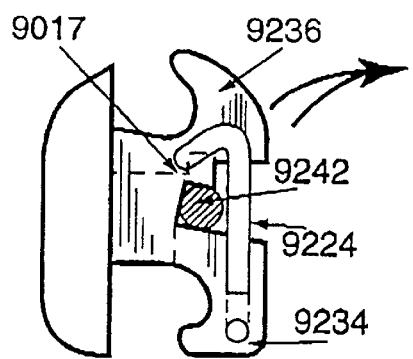
FIG. 85 is a side elevational view of the orthodontic bracket of FIG. 83 showing the initial release of the shutter.
Figure 86:
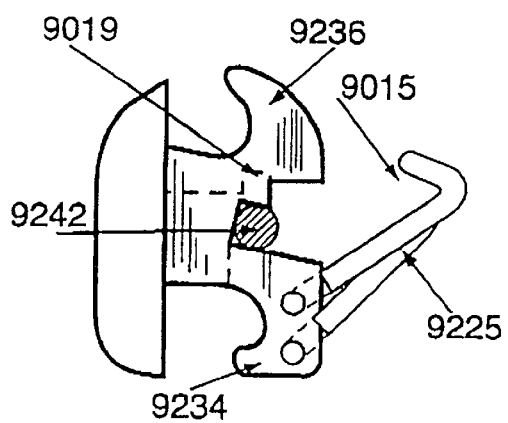
FIG. 86 is a side elevational view of the orthodontic bracket of FIG. 83 showing further movement of the shutter.

The wire 9001 between the arms 9009, 9011 is formed into a rearwardly-projecting look 9015 as can best be seen in FIG. 84 and is received within groove 9017. An extension 9019 is formed on the gingival surface of the body 9222 and passes through the hook 9015 when the shutter 9224 is in a closed position to provide a frictional fit between the hook 9015 and body 9222 and retain the shutter in the closed position.

Figure 87:
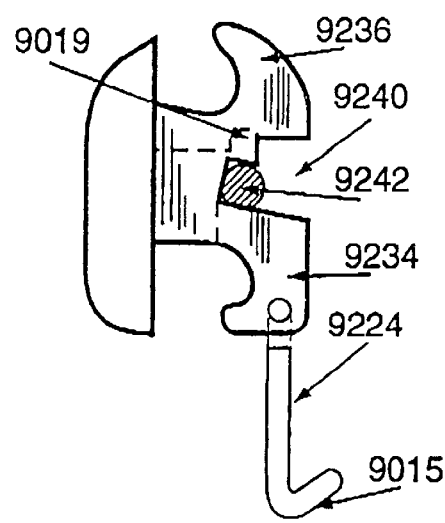
FIG. 87 is a side elevational view of the orthodontic bracket of FIG. 83 showing the shutter in a fully open position.

As shown in FIG. 84, the hook 9015 retains the shutter 9224 against the archwire 9242 and inhibits relative movement between the archwire and the body 9222 of the orthodontic bracket 9220. To release the archwire 9242, the shutter 9224 is caused to pivot about the offset tails 9003, 9005 to release the hook 9015 from the extension 9019. As the shutter 9224 is rotated, the eccentricity of the axes of rotation of the tails 9003, 9005 causes a torsional resistance due to flexure of the wire 9001 tending to return the shutter 9224 to the closed position. This movement is opposed until such time as the shutter 9224 goes over center, at which point the shutter 9224 becomes biased to the open position as shown in FIG. 87. In this way, the shutter 9224 is resiliently biased toward the body 9222 as it is moved towards the closed position but remains in a stable, open position at other times.

Figure 83:
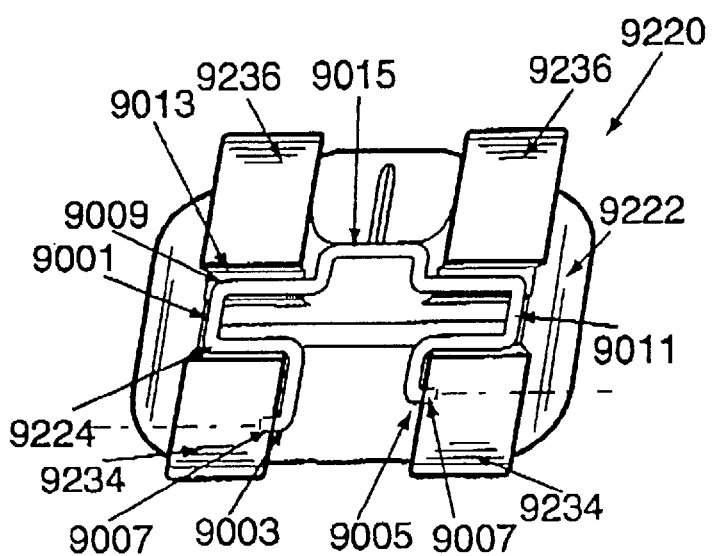
FIG. 83 is a front elevational view of yet another alternative embodiment of an orthodontic bracket in accordance with the present invention.
Figure 88:
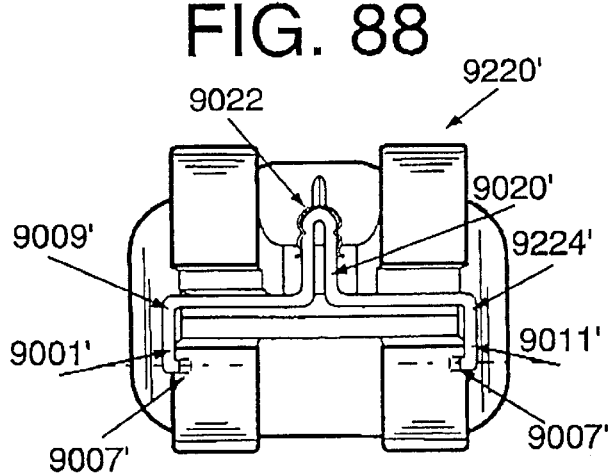
FIG. 88 is a front elevational view of yet another alternative embodiment of an orthodontic bracket in accordance with the present invention.
Figure 89:
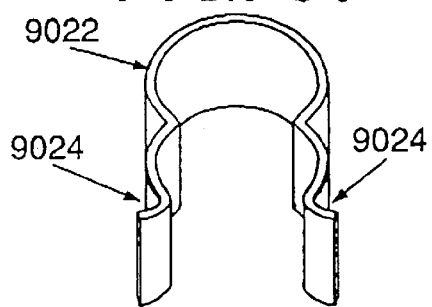
FIG. 89 is a perspective view of a component forming part of the orthodontic bracket of FIG. 88.

A further embodiment of an orthodontic bracket 9220' utilizing a wire for a shutter 9224' is shown in FIGS. 88 and 89, where like components of the previous embodiment will be described using like reference numerals with a suffix "'" added for clarity. In this embodiment, the shutter 9224' is formed from a wire 9001' having oppositely directed tails 9003', 9005'. Each of the tails 9003', 9005' is pivotally received within bores 9007' which are aligned on a common axis to allow free pivotal movement of the shutter 9224'. The bores may also be offset as shown in FIG. 83.

Figure 90:
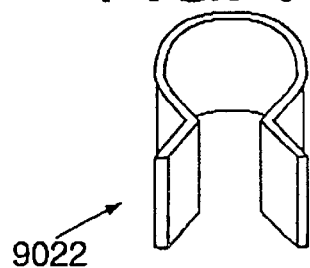
FIG. 90 is a perspective view of an alternative embodiment of the component of FIG. 89.

The wire 9001' between the arms 9009', 9011' is formed as an elongate U-shaped projection 9020 and is received within a locking clip 9022. As can best be seen in FIG. 89, locking clip 9022 is generally U-shaped with serpentine limbs terminating in outwardly-flared ends 9024. The projection 9020 may be received between the flared ends 9024 to force the limbs apart but is then resiliently retained between the limbs in a stable manner. The locking clip 9022 may alternatively have a generally circular section as shown in FIG. 90 but it is believed the clip 9022 shown in FIG. 89 facilitates insertion of the projection 9020. Again, the shutter 9224' retains the archwire 9242' within the archwire slot 9240' when the locking clip 9022 retains the shutter 9224' in a closed position.

Figure 91A:
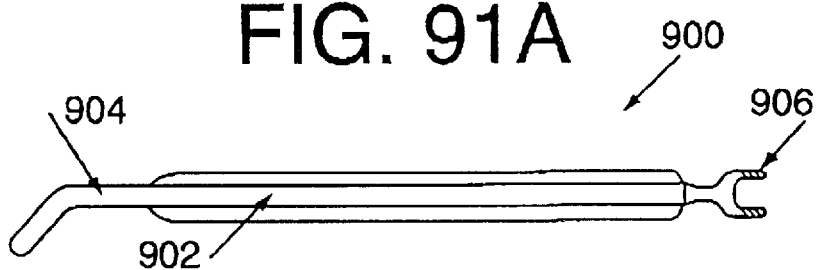
FIGS. 91a and 91b are side elevational views of embodiments of an orthodontic tool.
Figure 91B:
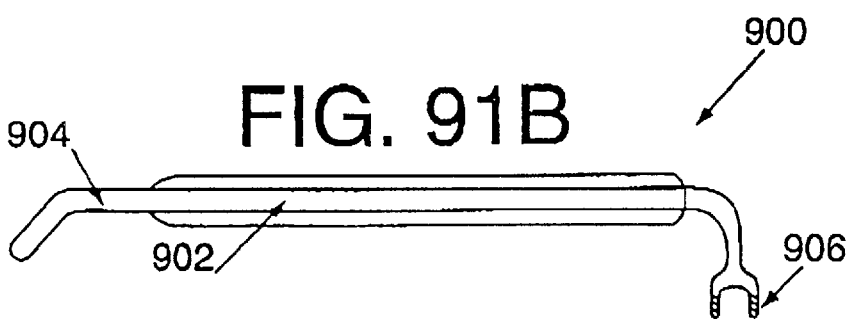

Referring now to FIGS. 91a and 91b, orthodontic tools 900 are shown which are suitable to open and close the shutters of the orthodontic brackets. As can be seen, each orthodontic tool 900 comprises a central body portion 902, a nose-shaped portion 904 at one end of the body portion for opening the shutter and a generally square corrugated fork-shaped portion 906 at the opposite end of the body portion 902 for gripping and guiding archwires lingually into the archwire slots to facilitate closure of the shutters. The fork-shaped portion straddles the outside of the bracket mesially and distally. In use, the nose-shaped portion 904 is inserted into the aperture in the shutter and a force is applied to the shutter using the tool 900 to move the shutter in the desired manned. In the embodiment of FIG. 91a, the fork-shaped portion 906 is aligned with the body portion 902, while in the embodiment of FIG. 91b, the fork-shaped portion 906 is at right angles to the body portion. Other angles between the body portion 902 and the fork-shaped portion 906 are of course suitable. Also, the shape of the nose-shaped portion 904 can vary to complement the aperture in the shutter.

Although a number of embodiments of orthodontic brackets have been disclosed, those of skill in the art will appreciate that other variations and/or modifications may be made to the present invention without departing from the scope thereof as defined by the appended claims.

I claim:

1. A pre-engaging orthodontic bracket for attaching an archwire to a tooth comprising:

a body having a lingual surface for attachment to a tooth, a pair of laterally spaced gingival tie wings and a pair of laterally spaced occlusal tie wings, said gingival and occlusal tie wings projecting from a labial surface of said body, said body defining two vertical passageways formed through said occlusal tie wings;

an archwire slot extending mesiodistally across said body and between the gingival and occlusal tie wings at opposed mesial and distal sides of said body to accommodate an archwire;

a locking shutter slidable in said passageways between an open position in which placement and removal of said archwire in said archwire slot is facilitated and a closed position in which placement and removal of said archwire in said archwire slot is inhibited; and biasing means located in each of said passageways and operable on said shutter for urging said shutter to said closed position and for releasably retaining the shutter in said closed position.

2. An orthodontic bracket as defined in claim 1 wherein each of said generally vertical passageways accommodates a spring to urge said shutter to said closed position and constitute said biasing means.

3. An orthodontic bracket as defined in claim 2 wherein said shutter includes a U-shaped strap having a pair of arms extending through said passageways and a bight bridging said arms below said occlusal tie wings, said bight acting as a handle to facilitate sliding movement of said shutter.

4. An orthodontic bracket as defined in claim 3 further comprising second retaining means to retain said shutter in said open position.

5. An orthodontic bracket as defined in claim 4 wherein said second retaining means is in the form of complimentary formations on said shutter and said generally vertical passageways.

6. An orthodontic bracket according to claim 1 further including a resilient shim having a first end attached to said shutter and a second end movable relative to said shutter the shim being engageable with an archwire in said archwire slot when said shutter is in said closed position, said resilient shim having a convex lingual surface resiliently urging said archwire into said archwire slot to provide a continuous corrective force thereon.

7. A pre-engaging orthodontic bracket for attaching an archwire to a tooth comprising:

a body having a lingual surface for attachment to a tooth, a pair of laterally spaced gingival tie wings and a pair of laterally spaced occlusal tie wings, said gingival and occlusal tie wings projecting from a labial surface of said body;

an archwire slot extending mesiodistally across said body and between the gingival and occlusal tie wings at opposed mesial and distal sides of said body to accommodate an archwire;

a locking shutter moveable relative to said body between an open position in which placement and removal of said archwire in said archwire slot is facilitated and a closed position in which placement and removal of said archwire in said archwire slot is inhibited; and a resilient shim having a first end attached to said shutter and a second end movable relative to said shutter, the shim being engageable with an archwire in said archwire slot when said shutter is in said closed position, said resilient shim having a convex lingual surface resiliently urging said archwire into said archwire slot to provide a continuous corrective force thereon.

8. A pre-engaging orthodontic bracket for attaching an archwire to a tooth comprising:

a body having a lingual surface for attachment to a tooth, a pair of laterally spaced gingival tie wings and a pair of laterally spaced occlusal tie wings, said gingival and occlusal tie wings projecting from a labial surface of said body, the body defining generally vertical slots formed in the occlusal tie wings;

an archwire slot extending mesiodistally across the said body and between the gingival and occlusal tie wings at opposed mesial and distal sides of said body to accommodate an archwire;

a locking shutter slidable between an open position in which placement and removal of said archwire in said archwire slot is facilitated and a closed position in which placement and removal of said archwire is inhibited, the shutter being slidable into said slots, said shutter further including a U-shaped strap having a pair of arms extending through said slots and a bight bridging said arms below said occlusal tie wings, said bight acting as a handle to facilitate sliding movement of said shutter; and a plurality of springs, each of the springs being located in one of said slots whereby the springs constitute retaining means operable upon said shutter to releasably retain said shutter in said closed position and whereby the springs also constitute biasing means to urge said shutter to said closed position.

9. An orthodontic bracket as defined in claim 8 further comprising a second retaining means to retain said shutter in said open position.

10. An orthodontic bracket as defined in claim 9 wherein said second retaining means is in the form of complementary formations on said shutter and said generally vertical slots.

* * * * *